(12) United States Patent
Takezawa

(10) Patent No.: US 11,814,488 B2
(45) Date of Patent: Nov. 14, 2023

(54) PRODUCTION METHOD AND PRODUCTION APPARATUS FOR DRIED VITRIGEL MEMBRANE

(71) Applicant: NATIONAL AGRICULTURE AND FOOD RESEARCH ORGANIZATION, Ibaraki (JP)

(72) Inventor: Toshiaki Takezawa, Tsukuba (JP)

(73) Assignee: NATIONAL AGRICULTURE AND FOOD RESEARCH ORGANIZATION, Ibaraki (JP)

( * ) Notice: Subject to any disclaimer, the term of this patent is extended or adjusted under 35 U.S.C. 154(b) by 986 days.

(21) Appl. No.: 16/613,254

(22) PCT Filed: Apr. 12, 2018

(86) PCT No.: PCT/JP2018/015373
§ 371 (c)(1),
(2) Date: Nov. 13, 2019

(87) PCT Pub. No.: WO2018/211876
PCT Pub. Date: Nov. 22, 2018

(65) Prior Publication Data
US 2021/0108035 A1 Apr. 15, 2021

(30) Foreign Application Priority Data

May 17, 2017 (JP) ................... 2017-098330

(51) Int. Cl.
| | |
|---|---|
| *C08J 3/075* | (2006.01) |
| *C08J 5/18* | (2006.01) |
| *C12M 1/12* | (2006.01) |
| *B29D 7/01* | (2006.01) |

(52) U.S. Cl.
CPC ............... *C08J 3/075* (2013.01); *B29D 7/01* (2013.01); *C08J 5/18* (2013.01); *C12M 25/14* (2013.01); *C08J 2389/06* (2013.01)

(58) Field of Classification Search
CPC ....... B29C 41/16; B29C 39/206; B29C 39/18; B29C 39/126; B29C 39/10; B29C 39/021;
(Continued)

(56) References Cited

U.S. PATENT DOCUMENTS

| | | | |
|---|---|---|---|
| 2005/0287573 A1* | 12/2005 | Stafslien | ................ C12M 33/00 |
| | | | 435/6.19 |
| 2013/0217126 A1 | 8/2013 | Takezawa et al. | |
| 2013/0280807 A1 | 10/2013 | Takezawa et al. | |

FOREIGN PATENT DOCUMENTS

| | | |
|---|---|---|
| CN | 102712763 A | 10/2012 |
| CN | 103619591 A | 3/2014 |

(Continued)

OTHER PUBLICATIONS

International Search Report (English) and Written Opinion dated Jul. 10, 2018, from International Application No. PCT/JP2018/015373, 8 pages.

(Continued)

*Primary Examiner* — Stella K Yi
(74) *Attorney, Agent, or Firm* — Meunier Carlin & Curfman LLC

(57) ABSTRACT

A production method for a dried Vitrigel film includes, in the following order: step 1 of concentrically arranging and disposing member A having one or more recesses and member B having one or more through holes, such that the recesses overlap the through holes; step 2 of pouring a sol from the through holes of member B; step 3 of gelling the sol; step 4 of drying and vitrifying the hydrogel obtained in step 3 in a state in which it is formed in the member A and the member B; step 5 of hydrating the dried hydrogel obtained in step 4; step 6 of drying and re-vitrifying the Vitrigel obtained in step 5; and step 7 of cutting off a portion, (Continued)

which slightly covers the top surface of the member A, of the dried Vitrigel obtained in step 6.

2 Claims, 4 Drawing Sheets

(58) Field of Classification Search
CPC ............... B29C 70/603; B29C 70/086; B29C 2037/0035; B29C 37/0032; C12M 25/14; C08J 5/18; C08J 3/075; B29D 7/01
See application file for complete search history.

(56) References Cited

FOREIGN PATENT DOCUMENTS

| | | |
|---|---|---|
| CN | 104144715 A | 11/2014 |
| JP | 2007-185107 | 7/2007 |
| JP | 4817847 | 11/2011 |
| JP | 2015-223108 | 12/2015 |
| JP | 5892611 | 3/2016 |
| JP | 5933223 | 6/2016 |
| TW | 200811286 A | 3/2008 |
| WO | 2014/208525 | 12/2014 |

OTHER PUBLICATIONS

Takezawa, "Development of new material "collagen vitrigel membrane" serving as foothold of cells, and its commercialization idea in medicine and pharmacy field" Journal of pharmaceutical science and technology, 2015, vol. 75, No. 6, pp. 344-353.
Search Report issued in CN Application No. 201880031208.6; dated Jul. 12, 2022; 9 pages.

* cited by examiner

DRIED VITRIGEL MEMBRANE
PET FILM

PRODUCTION METHOD AND PRODUCTION APPARATUS FOR DRIED VITRIGEL MEMBRANE

TECHNICAL FIELD

The present invention relates to a production method and a production apparatus for a dried Vitrigel membrane. Specifically, the present invention relates to a production method and a production apparatus for a dried Vitrigel membrane as well as a production method and a production apparatus for a device to which a dried Vitrigel membrane is adhered obtained using the production method and production apparatus.

Priority is claimed on Japanese Patent Application No. 2017-098330, filed May 17, 2017, the content of which is incorporated herein by reference.

BACKGROUND ART

Previously, the inventor developed a chamber provided with a dried collagen Vitrigel membrane (for example, refer to PTL 1). Initially, a dried collagen Vitrigel membrane having a smooth surface without wrinkles integrated with Parafilm (registered trademark) was produced (for example, refer to PTL 2), the film was attached to a cylindrical chamber body, and then the Parafilm (registered trademark) was peeled off to produce a chamber provided with a dried collagen Vitrigel membrane. At present, a collagen Vitrigel membrane pinched between two ring-shaped magnets is dried to produce a dried collagen Vitrigel membrane (for example, refer to PTL 3), the film is attached to a cylindrical chamber body, and then an unnecessary portion is removed to produce a chamber provided with the dried collagen Vitrigel membrane.

In addition, the inventor developed a method in which, in a chamber provided with a produced dried collagen Vitrigel membrane, a silicone-treated polyethylene terephthalate (PET) film is attached under the collagen Vitrigel membrane in order to prevent the collagen Vitrigel membrane from warping during hydration (for example, refer to PTL 4).

In addition, the inventor is currently developing a cell enclosure device provided with a dried collagen Vitrigel membrane. As the production method, first, a collagen Vitrigel membrane pinched between two ring-shaped magnets is dried to produce a dried collagen Vitrigel membrane (for example, refer to PTL 3). Next, the dried collagen Vitrigel membrane is attached to a ring-shaped side surface member and then an unnecessary portion is removed to obtain a cell enclosure device provided with the dried collagen Vitrigel membrane.

On the other hand, in an attachment-type (adhesive plaster-type) artificial skin preparation developed by the inventor, a dried atelocollagen Vitrigel membrane is placed on a wound and then a silicone-treated PET film with a size larger than the dried collagen Vitrigel membrane is overlaid thereon, and a dressing tape is further attached thereon as a cover (for example, refer to PTL 5).

CITATION LIST

Patent Literature

[PTL 1] Japanese Patent (Granted) Publication No. 5933223
[PTL 2] Japanese Patent (Granted) Publication No. 5892611
[PTL 3] Japanese Patent (Granted) Publication No. 4817847
[PTL 4] Japanese Unexamined Patent Application, First Publication No. 2015-223108
[PTL 5] Republished Japanese Translation No. 2014/208525 of the PCT International Publication for patent applications

DISCLOSURE OF INVENTION

Technical Problem

In a dried collagen Vitrigel membrane having a smooth surface without wrinkles and integrated with Parafilm (registered trademark) described in PTL 2, there is a problem in that, after peeling the Parafilm (registered trademark), components derived from the Parafilm (registered trademark) attach to the surface of the dried collagen Vitrigel membrane.

In addition, there are problems in that operations with the dried collagen Vitrigel membrane produced using the ring-shaped magnet described in PTL 3 are time-consuming and expensive and also in that dry wrinkles are generated in the dried collagen Vitrigel membrane.

In addition, in a chamber provided with a collagen Vitrigel membrane to which the silicone-treated PET film described in PTL 4 is attached, the silicone-treated PET film is attached after the chamber provided with the collagen Vitrigel membrane is produced. Therefore, a technique is yet to be developed for producing a dried collagen Vitrigel membrane having a smooth surface without wrinkles, to which a silicone-treated PET film is weakly attached, at a low cost and in a simple manner.

The present invention was made in consideration of the above circumstances and provides a production method and a production apparatus for a dried Vitrigel membrane, which are able to obtain a dried Vitrigel membrane having a smooth surface without wrinkles in a simple manner. In addition, the present invention also provides a simple production method and a production apparatus for a device to which a dried Vitrigel membrane is adhered, with which continuous production from the production of the dried Vitrigel membrane is possible.

Solution to Problem

As a result of intensive research to achieve the object described above, the inventor found that using a device provided with a member having low adsorptivity to a hydrogel and a member having high adsorptivity to a hydrogel makes it possible to obtain a dried Vitrigel membrane having a smooth surface without wrinkles in a simple manner, thereby completing the present invention.

That is, the present invention includes the following aspects.

According to a first aspect of the present invention, there is provided a production method for a dried Vitrigel membrane, the method including, in the following order: step 1 of concentrically arranging and disposing a member A, which has one or more recesses and in which, in a bottom surface of the recess, a central part is formed of a first material having low adsorptivity to a hydrogel and a peripheral part is formed of a second material having high adsorptivity to a hydrogel, and a member B having one or more through holes with a cross-section of substantially equal size to a cross-section of the recess of the member A, such that the recess of the member A and the through hole of the member B overlap, step 2 of pouring a sol from the through holes of member B, step 3 of gelling the sol by leaving the member A and the member B in which the sol is poured to stand, step 4 of drying and vitrifying a hydrogel obtained in step 3 in a state in which it is formed in the member A and the member B, step 5 of hydrating the dried hydrogel obtained in step 4 in a state in which it is formed in the member A and the member B, step 6 of drying and re-vitrifying the Vitrigel obtained in step 5 in a state in which it is formed in the member A and the member B, and step 7 of cutting off a portion slightly covering a top surface of the member A, from the dried Vitrigel obtained in step 6.

In the production method for a dried Vitrigel membrane according to the first aspect, the first material may be removable at the bottom surface of the recess of the member A.

According to a second aspect of the present invention, there is provided a production method for a device to which a dried Vitrigel membrane is adhered, which uses the dried Vitrigel membrane obtained by the production method for a dried Vitrigel membrane according to the first aspect, the method including, in the following order: step 8 of separating the member B from the member A in a state in which the dried Vitrigel membrane is present in the member A and the member B, concentrically arranging a member C having one or more recesses with a cross-section of substantially equal size to a cross-section of the recess of the member A, in which a cylindrical member having an adhesive layer on a peripheral part of a surface on the side in contact with the dried Vitrigel membrane is detachably inserted, such that the recesses of the member A and the recesses of the member C overlap, and disposing the member A on the member C, and step 9 of separating the member A and the member C and extracting the cylindrical member to which the dried Vitrigel membrane is adhered from the member A.

The production method for a device to which a dried Vitrigel membrane is adhered according to the second aspect may further include, in the following order after step 9: step 10 of detachably inserting the cylindrical member to which the dried Vitrigel membrane obtained in step 9 is adhered to a second member C such that the surface to which the dried Vitrigel membrane is adhered is in contact with a bottom surface of the second member C and forming an adhesive layer on a peripheral part of a surface of the cylindrical member to which the dried Vitrigel membrane is not adhered, step 11 of separating a second member B from a second member A in a state in which a second dried Vitrigel membrane obtained by the production method for a dried Vitrigel membrane is formed in the second member A and the second member B, concentrically arranging the second member C obtained in step 10 such that the recess of the second member A and the recess of the second member C overlap, and disposing the second member A on the second member C such that the adhesive layer on the surface of the second member C to which the dried Vitrigel is not adhered and the second dried Vitrigel formed in the second member A are in contact, and step 12 of separating the second member C and the second member A and extracting the cylindrical member to which the dried Vitrigel membrane is adhered to both of the surfaces from the second member A.

According to a third aspect of the present invention, there is provided a production apparatus for a dried Vitrigel membrane including a member A, which has one or more recesses and in which, in a bottom surface of each of the recesses, a central part is formed of a first material having low adsorptivity to a hydrogel and a peripheral part is formed of a second material having high adsorptivity to a hydrogel, and a member B having one or more through holes with a cross-section of substantially equal size to a cross-section of the recesses of the member A, in which, when the member A and the member B are concentrically arranged, the recesses and the through holes are arranged to overlap.

In the production apparatus for a dried Vitrigel membrane according to the third aspect, the first material may be removable at the bottom surface of the recess of the member A.

According to a fourth aspect of the present invention, there is provided a production apparatus for a device to which a dried Vitrigel membrane is adhered including the production apparatus for a dried Vitrigel membrane according to the third aspect, and a member C having one or more recesses with a cross-section of substantially equal size to a cross-section of the recess of the member A, in which the recess of the member C is for detachably inserting a cylindrical member which is a main part of a device to which a dried Vitrigel membrane is adhered and, when the member A and the member C are concentrically arranged, the recess of the member A and the recess of the member C are arranged to overlap.

The production apparatus for a device to which a dried Vitrigel membrane is adhered according to the aspect described above may be provided with two or more production apparatuses for a dried Vitrigel membrane.

Advantageous Effects of Invention

According to the production method and production apparatus for a dried Vitrigel membrane of the above aspects, it is possible to obtain a dried Vitrigel membrane having a smooth surface without wrinkles in a simple manner. In addition, according to the production method and production apparatus for a device to which the dried Vitrigel membrane of the above aspect is adhered, it is possible to continuously produce a device to which a dried Vitrigel membrane is adhered from the production of the dried Vitrigel membrane, and to obtain a device to which a dried Vitrigel membrane is adhered in a simple manner.

BEST MODE FOR CARRYING OUT THE INVENTION

<<Production Method for Dried Vitrigel Membrane>>

Figure 1A:
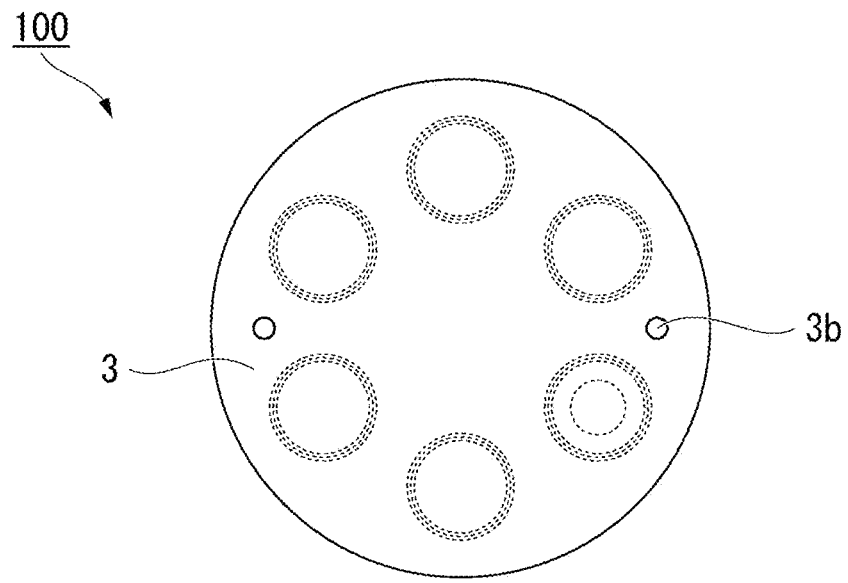
FIG. 1A is a plan view showing an example of a production apparatus for a device to which a dried Vitrigel membrane is adhered of the present embodiment.

The production method for a dried Vitrigel membrane of the present embodiment is a method using a member A and a member B. The member A has one or more recesses. In a bottom surface of the recess, a central part is formed of a first material having low adsorptivity to a hydrogel and a peripheral part is formed of a second material having high adsorptivity to a hydrogel. In addition, the member B has one or more through holes with a cross-section of substantially equal size to a cross-section of the recess of the member A. In addition, the production method for a dried Vitrigel membrane of the present embodiment is provided with the following steps 1 to 7 in this order. In step 1, the recess of the member A and the through hole of the member B are concentrically arranged and disposed so as to overlap. In step 2, a sol is poured from the through holes of the member B. In step 3, the sol is gelled by leaving the member A and the member B in which the sol was poured to stand. In step 4, a hydrogel obtained in step 3 is dried and vitrified in a state in which it is formed in the member A and the member B. In step 5, the dried hydrogel obtained in step 4 is hydrated in a state in which it is formed in the member A and the member B. In step 6, the Vitrigel obtained in step 5 is dried and re-vitrified in a state in which it is formed in the member A and the member B. In step 7, a portion slightly covering a top surface of the member A is cut off from the dried Vitrigel obtained in step 6.

According to the production method for a dried Vitrigel membrane of the present embodiment, it is possible to produce a dried Vitrigel membrane having a smooth surface without wrinkles in a simple manner.

In the present specification, "sol" means a solution formed of colloidal particles (size: approximately 1 to several hundred nm) of a dispersoid using a liquid as a dispersion medium, in particular, a polymer compound. More specifically, examples of the sol include aqueous solutions of natural product polymer compounds and synthetic polymer compounds. Therefore, in a case where these polymer compounds form a network structure due to the introduction of cross-linking by chemical bonding, the sol is converted into a "hydrogel", which is a substance in a semisolid state which contains a large amount of water in the network. That is, "hydrogel" means the gelled sol. In addition, "Vitrigel" indicates a gel in a stable state obtained by rehydration after vitrification of a hydrogel known in the related art, which the inventors named "Vitrigel (registered trademark)". In addition, when using the term "Vitrigel" below, the term "(registered trademark)" is omitted.

In addition, in the present specification, when explaining in detail the steps for producing a dried Vitrigel membrane formed of a hydrogel, a dried body of the hydrogel immediately after the vitrification step that has not yet been subjected to a rehydration step is simply referred to as a "dried hydrogel". Here, the gel obtained by passing through the rehydration step after the vitrification step is distinguished and referred to as "Vitrigel" while the dried body obtained by vitrifying the Vitrigel is referred to as "dried Vitrigel." In addition, a product obtained by subjecting dried Vitrigel to a step of applying ultraviolet irradiation is referred to as "Vitrigel material obtained by subjecting dried Vitrigel to an ultraviolet irradiation process", a gel obtained by subjecting the Vitrigel material to a rehydration step is referred to as a "Vitrigel material", and a dried body obtained by drying the Vitrigel material is referred to as a "dried body of a Vitrigel material". Accordingly, the "Vitrigel" and "Vitrigel material" are hydrates.

A detailed description will be given below of each step of the production method for a dried Vitrigel membrane of the present embodiment.

<Step 1>

First, the member B is disposed on the member A. At this time, recesses of the member A and through holes of the member B are concentrically arranged so as to overlap. When the recesses of the member A and the through holes of the member B overlap and communicate with each other, in the subsequent step 2, it is possible to pour the sol into the recesses of the member A through the through holes of the member B.

Next, the configuration and materials of each member are shown below.

[Member A]

(Shape)

The member A has one or more recesses. In this recess, a dried Vitrigel membrane is produced.

To be able to obtain a dried Vitrigel membrane having a smooth surface, the recess of the member A has a smooth bottom surface and a side surface and a bottom surface are perpendicular to each other.

In addition, it is possible to set the area of the cross-section of the recess to a size for a dried Vitrigel membrane of a desired size, without particular limitation. Specifically, it is possible to set the area of the cross-section of the recess to, for example, 4 mm$^2$ or more and 400 cm$^2$ or less, for example, 20 mm$^2$ or more and 40 cm$^2$ or less, for example, 80 mm$^2$ or more and 4 cm$^2$ or less.

The number of recesses is, for example, 1, 2, 3, 4, 5, 6, 7, 8, 9, 10, 12, 15, 20, or the like, without being limited thereto. Among the above, the number of recesses is preferably an even number, more preferably 2, 4, 6, or 8, and even more preferably 4, 6, or 8.

In addition, in a case where the member A has two or more recesses, the recesses are preferably arranged at equal intervals on the member A.

In addition, in the member A, it is possible to appropriately adjust the depth of the recess such that the thickness of the dried Vitrigel membrane is a desired thickness and the depth is preferably 1 µm or more and 5 mm or less, more preferably 5 µm or more and 3 mm or less, even more preferably 10 µm or more and 2 mm or less, and particularly preferably 100 µm or more and 1 mm or less. When the depth of the recess is in the ranges described above, for example, in a case where the dried Vitrigel membrane obtained by the production method of the present embodiment is used for a cell enclosure device, it is possible to obtain a strength at which it is possible to pour cells into the device and carry out culturing.

In addition, in the member A, it is possible to appropriately adjust the shape of the cross-section of the recess such that the shape of the dried Vitrigel membrane is a desired shape and examples thereof include polygons such as triangles, quadrilaterals (including squares, rectangles, and trapezoids), pentagons, hexagons, heptagons, and octagons; circles, approximate circles, ovals, approximate ovals, semicircles, fan shapes, and the like, without being limited thereto. Among the above, the shape of the cross-section of the recess is preferably circular.

In addition, in the member A, in a case where the cross-section of the recess is circular, it is possible to appropriately adjust the diameter thereof such that the diameter of the dried Vitrigel membrane is a desired diameter and, for example, it is possible to set the diameter to 2 mm or more and 226 mm or less, for example, 5 mm or more and 72 mm or less, and, for example, 10 mm or more and 23 mm or less.

(Material)

In addition, as a material forming the member A, in a bottom surface of the recess, a central part is formed of a first material having low adsorptivity to a hydrogel and a peripheral part is formed of a second material having high adsorptivity to a hydrogel. In addition, all portions other than the central part of the bottom surface of the recess may be formed of the second material.

Here, "the central part of the bottom surface of the recess" means, for example, a position 9/10, preferably 4/5, more preferably 3/4, even more preferably 2/3, and particularly preferably 1/2 of the distance from the center of the bottom surface to the shortest edge portion. In addition, "the peripheral part of the bottom surface of a recess" means a portion which surrounds the central part of the bottom surface of the recess.

In the present specification, "a material having low adsorptivity to a hydrogel" means a material which does not adsorb a hydrogel at all or a material which adsorbs with a weak force to be removable.

In addition, in the present specification, the "a material having high adsorptivity to a hydrogel" means a material which completely adsorbs the hydrogel or a material which adsorbs with a strong force at which removal is not possible.

Specifically, it is possible to use the definitions shown below. First, when the hydrogel is brought in contact with the first material or the second material and the hydrogel on the surface of the first material or the second material is observed from the horizontal direction, if the intersection point between the contour curve of the hydrogel and the surface of the first material or the second material is the "end point", a contact angle $\theta$ is measured at the end point. At this time, at the end point, the surface tension $\gamma S1$ or $\gamma S2$ of the first material or the second material (interfacial tension between the gas/the first material or the second material), the interfacial tension $\gamma LS1$ or $\gamma LS2$ between the hydrogel/the first material or the second material, and the surface tension $\gamma L$ of the hydrogel (interfacial tension between the gas/the hydrogel) are applied. When the wetting state is stable, the end point is stationary without moving to the right or left, and thus the three forces of "$\gamma S1$, $\gamma LS1$, and $\gamma L$" or "$\gamma S2$, $\gamma LS2$, and $\gamma L$" are balanced. The balance between these three forces is shown by the equation (Young's equation) represented by [1] or [2] below.

$$\gamma S1 = \gamma L \cos\theta + \gamma LS1 \quad [1]$$

$$\gamma S2 = \gamma L \cos\theta + \gamma LS2 \quad [2]$$

In addition, the wettability, that is, the magnitude of the contact angle, is determined by the surface properties of each of the hydrogel and the first material or the second material. Thus, it is possible to consider using equation [3] which is a modification of equation [1] or equation [4] which is a modification of equation [2].

$$\cos\theta = (\gamma S1 - \gamma LS1)/\gamma L \quad [3]$$

$$\cos\theta = (\gamma S2 - \gamma LS2)/\gamma L \quad [4]$$

cos $\theta$ decreasing and approaching 0 means that the contact angle $\theta$ approaches 180° and the wetting becomes worse, that is, the adsorptivity to the hydrogel decreases. From this, examples of a method for reducing the adsorptivity to the hydrogel include methods of either "(1) increasing the surface tension $\gamma L$ of the hydrogel" or "(2) decreasing the surface tension $\gamma S1$ of the first material".

On the other hand, cos $\theta$ increasing and approaching 1 means that the contact angle $\theta$ approaches 0° and the wetting becomes better, that is, the adsorptivity to the hydrogel becomes high. From this, examples of a method for increasing the adsorptivity to the hydrogel include methods of either "(1) decreasing the surface tension $\gamma L$ of the hydrogel" or "(2) increasing the surface tension $\gamma S2$ of the second material".

The variable range of the surface tension of the hydrogel is limited in order to make the strength of the obtained membrane constant. Therefore, in the case of reducing the adsorptivity to the hydrogel, the method of "(2) decreasing the surface tension $\gamma S1$ of the first material" is suitable. On the other hand, in the case of increasing the adsorptivity to the hydrogel, the method of "(2) increasing the surface tension $\gamma S2$ of the second material" is suitable.

From the above, a material having low adsorptivity to a hydrogel is a material in which a surface tension is smaller than the surface tension of the hydrogel. More specifically, it is possible to reduce the surface tension of the first material by, for example, 1 dyne/cm or more than the surface tension of the hydrogel, preferably 5 dynes/cm or more, more preferably 10 dynes/cm or more, even more preferably 20 dynes/cm or more, and particularly preferably 30 dynes/cm or more.

Making the surface tension of the first material smaller than the surface tension of the hydrogel with the lower limit value described above or more makes it possible to easily peel off the produced dried Vitrigel membrane from the first material.

In addition, a material having high adsorptivity to a hydrogel is a material having a surface tension larger than the surface tension of the hydrogel. More specifically, the surface tension of the second material is, for example, 1 dyne/cm or more than the surface tension of the hydrogel, preferably 3 dynes/cm or more, more preferably 5 dynes/cm or more, even more preferably 7 dynes/cm or more, and particularly preferably 10 dynes/cm or more.

Making the surface tension of the second material greater than the surface tension of the hydrogel with the lower limit value described above or more makes it possible to suppress the produced dried Vitrigel membrane from unintentionally warping and peeling or moving after the step 7 described below.

In addition, in a case where the hydrogel is a gel including a protein such as collagen, the material having low adsorptivity to the hydrogel may be a material having many hydrophilic groups on the surface and the material having high adsorptivity to the hydrogel may be a material having many hydrophobic groups on the surface. It is possible to appropriately adjust the numbers of the hydrophilic groups and the hydrophobic groups on the surface according to the type of the hydrogel including the protein to be used.

Examples of the hydrophilic groups include a phosphoryl choline group, an alkylene glycol group, and the like.

Examples of the hydrophobic groups include linear, branched, and cyclic alkyl groups. The number of carbon atoms of the alkyl group is, for example, 1 or more and 20 or less, and, for example, 4 or more and 20 or less.

Specific examples of the first material include stainless steel, poly(vinyl chloride), and the like, without being limited thereto. In addition, as the first material, for example, a film on which a release agent such as silicone is laminated may be used. Producing the dried Vitrigel membrane such that the dried Vitrigel membrane and the surface on which the release agent layer of the film is laminated are in contact with each other makes it possible to easily peel off the dried Vitrigel membrane. Examples of the material of the film include polyethylene, polyethylene terephthalate, polystyrene, polypropylene, and the like, without being limited thereto. In addition, as the first material, for example, an oil film formed by coating an oil such as silicone on the bottom surface of the member A may be used.

Specific examples of the second material include glass materials, polyacrylates (acrylic resins), polystyrenes, nylons, and the like, without being limited thereto. More specifically, examples of the glass material include soda lime glass, Pyrex (registered trademark) glass, Vycor (registered trademark) glass, quartz glass, and the like.

More specific examples of the polyacrylate (acrylic resin) include poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), and the like.

In addition, all portions other than the central part of the bottom surface of a recess may be formed of the second material described above.

In addition, the first material may be removably disposed on the bottom surface of the recess of the member A. At this time, the first material is preferably adhered to the material forming the bottom surface of the recess of the member A with a weak force with which it can be easily removed by being physically torn off. Specifically, for example, as shown in the Production Example described below, the first material may be adhered to the material forming the bottom surface of the recess of the member A with a weak force by which it can be easily removed by being physically torn off with tweezers or the like via a salt such as PBS. Alternatively, the first material may be adhered to the material forming the bottom surface of the recess of the member A with a weak force to be easily removable by being physically torn off with tweezers or the like via a release agent layer containing a release agent such as silicone.

At this time, examples of the material forming the bottom surface of the recess of the member A present below the first material include the same material as the second material described above.

[Member B]
(Shape)

The member B has one or more through holes. The through hole is of substantially equal size to the cross-section of the recess of the member A. Specifically, the area of the cross-section of the through hole is preferably 1 or more and 1.5 or less, more preferably 1 or more and 1.3 or less, even more preferably 1 or more and 1.25 or less, and particularly preferably 1.21 times the area of the cross-section of the recess of the member A.

The number of through holes is preferably the same number as the number of recesses in the member A, for example, 1, 2, 3, 4, 5, 6, 7, 8, 9, 10, 12, 15, 20, or the like, without being limited thereto. Among these, the number of through holes is preferably an even number, more preferably 2, 4, 6, or 8, and even more preferably 4, 6, or 8.

In addition, in a case where the member B has two or more through holes, the through holes are preferably arranged at equal intervals on the member B. In addition, in a case where the member B has two or more through holes, the through holes are arranged on the member B at the same intervals as the recesses on the member A. In addition, when the member A and the member B are concentrically arranged, the through holes of the member B are arranged so as to overlap with the recesses of the member A.

In addition, in the member B, it is possible to set the height of the through hole to, for example, 1 μm or more to 100 mm or less, for example, 1 μm or more to 50 mm or less, for example, 5 μm or more to 10 mm or less, and, for example, 10 μm or more and 5 mm or less, without being limited thereto.

In addition, in the member B, it is possible to set the shape of the cross-section of the through hole to be the same as the cross-section of the recess of the member A, for example, polygons such as triangles, quadrilaterals (including squares, rectangles, and trapezoids), pentagons, hexagons, heptagons, and octagons; circles, approximate circles, ovals, approximate ovals, semicircles, fan shapes, and the like, without being limited thereto. Among the above, the shape of the cross-section of the through hole is preferably circular.

In addition, in the member B, in a case where the cross-section of the through hole is circular, it is possible to set the diameter thereof to be substantially the same as the diameter of the recess of the member A, for example, 2 mm or more and 226 mm or less, for example, 5 mm or more and 72 mm or less, and, for example, 10 mm or more and 23 mm or less.

(Material)

In addition, the material of the member B is not particularly limited and is preferably the same as the second material forming the member A for ease of handling. Examples of the material of the member B include the same materials which were illustrated as the second material of the member A described above.

<Step 2>

Next, the sol is poured into the recess of the member A from the through hole of the member B. Examples of the sol encompass natural polymer compounds such as components derived from an extracellular matrix available for gelation, fibrin, agar, agarose, and cellulose, and synthetic polymer compounds such as polyacrylamide, polyvinyl alcohol, polyethylene oxide, and poly(II-hydroxyethylmethacrylate)/polycaprolactone, and the like. Examples of components derived from the extracellular matrix available for gelation include collagen (type I, type II, type III, type V, type XI, and the like), basement membrane components (trade name: Matrigel) reconstituted from mouse EHS tumor extract (including type IV collagen, laminin, heparan sulfate proteoglycan, and the like), glycosaminoglycan, hyaluronic acid, proteoglycan, gelatin, and the like, without being limited thereto. It is possible to produce a desired dried Vitrigel membrane by selecting each of the components suitable for gelation such as salts, the concentrations, the pH thereof, and the like. In addition, combining the raw materials makes it possible to obtain a dried Vitrigel membrane which mimics various in vivo tissues. Among the above, as the sol, a component derived from an extracellular matrix available for gelation is preferable, and collagen is more preferable. In addition, examples of more preferable materials among collagens include native collagen or atelocollagen.

In a case where the sol is a collagen sol, as a collagen sol having an optimal salt concentration, for example, it is possible to use a collagen sol prepared using physiological saline, phosphate buffered saline (PBS), Hank's Balanced Salt Solution (HBSS), a basic culture medium, a serum-free culture medium, a serum-containing culture medium, or the like. In addition, it is possible to set the pH of the solution at the time of collagen gelation, for example, to 6 or more and 8 or less.

In particular, in a case where a serum-free culture medium is used, it is possible to avoid including substances, which are not suitable for transplantation and which are included in serum components of other animals (for example, antigens, pathogenic factors, or the like), in the dried Vitrigel membrane. Therefore, the dried Vitrigel membrane obtained using a serum-free culture medium is suitably used for a medical cell transplantation device.

In addition, the concentration of collagen sol for producing a dried Vitrigel membrane is preferably 0.1% or more and 1.0% or less, and more preferably 0.2% or more and 0.6% or less. When the concentration of the collagen sol is the above lower limit value or more, the gelation is not excessively weak, and when the concentration of the collagen sol is the above upper limit value or less, it is possible to obtain a dried Vitrigel membrane formed of uniform collagen gel.

In addition, the collagen sol may be prepared at approximately 4° C., for example.

<Step 3>

Next, the member A and member B into which the sol is poured are left to stand to gel the sol.

It is possible to appropriately adjust the temperature at which the sol is kept according to the type of sol being used. For example, in a case where the sol is a collagen sol, it is possible to set the temperature during gelation to a temperature lower than the denaturation temperature of collagen depending on the animal species of the collagen used, and generally, it is possible to perform gelation for several minutes to several hours by keeping the temperature at 20° C. or higher and 37° C. or lower.

<Step 4>

Next, the obtained hydrogel is dried and vitrified in a state in which it is formed in the member A and the member B.

Drying the hydrogel makes it possible to completely remove the free water in the hydrogel and to further proceed with partial removal of bonding water.

As the period of this vitrification step (the step of completely removing the free water in the hydrogel and then proceeding to partially remove the bonding water) is lengthened, it is possible to obtain Vitrigel with superior transparency and strength at the time of rehydration. After a short period of vitrification, it is also possible to wash the Vitrigel obtained by rehydration with PBS or the like and carry out the vitrification again as necessary.

As a drying method, for example, it is possible to use various methods such as air drying, drying in a sealed container (circulating air in a container or constantly supplying dry air), drying in an environment in which silica gel is placed, and the like. For example, examples of methods of air drying include methods such as drying for 2 days in an incubator kept sterile at 10° C. and 40% humidity, or drying in a clean bench in a sterile state for one whole day at room temperature.

<Step 5>

Next, the obtained dried hydrogel is hydrated in the state in which it is formed in the member A and the member B. At this time, it is possible to carry out the hydration using physiological saline, phosphate buffered saline (PBS), or the like.

<Step 6>

Next, the obtained Vitrigel is dried and re-vitrified in the state in which it is formed in the member A and the member B.

Examples of the drying method include the same methods as the methods illustrated in step 4 described above.

<Step 7>

Next, in the obtained dried Vitrigel, a portion of the dried Vitrigel which slightly covers the top surface of the member A is cut off using, for example, a cylindrical blade (thin blade) or the like. At this time, a cylindrical blade is punched in along the inner side surface of the member B and the dried Vitrigel slightly covering the top surface of the member A is cut off. This makes it possible to form a dried Vitrigel having a cross-section size which is substantially uniform. It is possible to set the cross-section of the cylindrical blade to a size slightly larger than the cross-section of the recess of the member A and slightly smaller than the cross-section of the through hole of the member B. Specifically, the area of the cross-section of the cylindrical blade is preferably 1 times or more and 1.15 times or less, more preferably 1 times or more and 1.1 times or less, even more preferably 1 times or more and 1.07 times or less, and particularly preferably 1 times or more and 1.05 times or less the area of the cross-section of the recess of the member A.

In addition, it is possible to set the height of the cylindrical blade to a height at which insertion into the member A and member B and cutting off of the produced dried Vitrigel membrane are possible, without particular limitation.

In addition, it is possible for the shape of the cross-section of the cylindrical blade to be the same as the cross-section of the recess of the member A, for example, polygons such as triangles, quadrilaterals (including squares, rectangles, and trapezoids), pentagons, hexagons, heptagons, and octagons; circles, approximate circles, ovals, approximate ovals, semicircles, fan shapes, and the like, without being limited thereto. Among the above, the shape of the cross-section of the through hole is preferably circular.

In addition, in a case where the cylindrical blade has a circular cross-section, it is possible to set the diameter of the cylindrical blade to be substantially the same as the diameter of the recess of the member A, for example, 2 mm or more and 226 mm or less, for example, 5 mm or more and 72 mm or less, and, for example, 10 mm or more and 23 mm or less.

In addition, for example, in the case of producing two or more dried Vitrigel membranes at the same time, when a member D is provided with cylindrical blades in a number corresponding to the number of recesses of the member A, and the member A, the member B, and the member D are concentrically arranged, two or more dried Vitrigel membranes produced in the recess of member A may be cut off at one time using the member D in which a cylindrical blade is arranged such that the recess of the member A and the cylindrical blade overlap via the through hole of the member B.

<Other Steps>

In addition, the obtained dried Vitrigel may be irradiated with ultraviolet rays in a state in which it is formed in the member A and the member B after step 6 and before step 7 or in a state in which it is extracted from the member A and the member B after step 7 to obtain a Vitrigel material obtained by subjecting dried Vitrigel to an ultraviolet irradiation process.

For ultraviolet irradiation, it is possible to use a known ultraviolet irradiation device.

As the irradiation energy of the ultraviolet rays on the dried Vitrigel, the total irradiation amount per unit area is preferably 0.1 $mJ/cm^2$ or more and 6000 $mJ/cm^2$ or less, more preferably 10 $mJ/cm^2$ or more and 4000 $mJ/cm^2$ or less, and even more preferably 100 $mJ/cm^2$ or more and 3000 $mJ/cm^2$ or less. When the total irradiation amount is in the above range, it is possible for the transparency and strength of Vitrigel material obtained in the subsequent rehydration step to be particularly preferable.

In addition, the irradiation of the dried Vitrigel with ultraviolet rays may be repeated a plurality of times. In the case of repeating the irradiation of the dried Vitrigel with ultraviolet rays, after the irradiation of the first ultraviolet rays, it is preferable for the steps of rehydration and re-vitrification of the Vitrigel material obtained by subjecting dried Vitrigel to an ultraviolet irradiation process to be performed and then for the dried body of Vitrigel material after re-vitrification to be irradiated with ultraviolet rays second and subsequent times.

When the total ultraviolet irradiation amount per unit area is the same, the irradiation of the dried Vitrigel with ultraviolet rays is repeatedly performed by being divided into a plurality of times, such that it is possible to further increase the transparency and strength of the Vitrigel material obtained by rehydration. In addition, the larger the number of divisions, the better. For example, when the total irradiation amount per unit area of the ultraviolet irradiation on the dried Vitrigel is in the range of 1000 mJ/cm$^2$ or more and 4000 mJ/cm$^2$ or less, the number of irradiation performed in the above range is preferably 2 times or more and 10 times or less, and more preferably 2 times or more and 6 times or less.

In addition, in a case where the irradiation of the dried Vitrigel with ultraviolet rays is repeated, irradiation is carried out with the irradiation site of the ultraviolet rays divided into one surface and the other surface (upper surface and lower surface) of the dried Vitrigel, and the total irradiation amount may be set as the total ultraviolet irradiation amount per unit area on the dried Vitrigel.

The reason the strength and transparency of the Vitrigel material obtained by further rehydration are increased by irradiating the dried Vitrigel with ultraviolet rays is considered to be because the polymer compounds in the Vitrigel material are cross-linked by the ultraviolet rays. That is, this operation is considered to make it possible to maintain high transparency and strength in the Vitrigel material.

Furthermore, the Vitrigel material obtained by subjecting dried Vitrigel to an ultraviolet irradiation process may be rehydrated to obtain the Vitrigel material. At this time, it is possible to perform the hydration using physiological saline, phosphate buffered saline (PBS), or the like.

Furthermore, a dried body of Vitrigel material may be obtained by drying the obtained Vitrigel material and carrying out re-vitrification.

Examples of the drying method include the same methods as the methods illustrated in step 4 described above.

It is possible to use the dried Vitrigel membrane obtained by the production method for a dried Vitrigel membrane of the present embodiment for, for example, a chamber provided with a dried Vitrigel membrane, a cell enclosure device provided with a dried Vitrigel membrane, adhesive artificial skin preparations using a film provided with a dried Vitrigel membrane, and the like.

<<Production Method for Device to which Dried Vitrigel Membrane is Adhered>>

First Embodiment

The production method for a device to which the dried Vitrigel membrane is adhered of the present embodiment is a production method for a device to which the dried Vitrigel membrane is adhered, which uses the dried Vitrigel membrane obtained by the production method for a dried Vitrigel membrane according to the embodiment described above. Besides, in addition to the member A and the member B, the production method for a device to which the dried Vitrigel membrane is adhered of the present embodiment also uses a member C. The member C has one or more recesses. In the recess of this member C, a cylindrical member having an adhesive layer at the peripheral part of the surface on the side in contact with the dried Vitrigel membrane is detachably inserted. In addition, the cross-section of the recess of the member C is of substantially equal size to a cross-section of the recess of the member A. In addition, the production method for a device to which the dried Vitrigel membrane is adhered of the present embodiment is a method including step 8 and step 9 below in this order. In step 8, the member B is separated from the member A in a state in which the dried Vitrigel membrane is arranged in the member A and the member B, then the member C is concentrically arranged such that the recess of the member A and the recess of the member C overlap, and the member A is disposed on the member C. In step 9, the member A and the member C are separated and the cylindrical member to which the dried Vitrigel membrane is adhered is extracted from the member A.

According to the production method for a device to which the dried Vitrigel membrane is adhered of the present embodiment, it is possible to continuously produce a device to which the dried Vitrigel membrane is adhered from the production method for a dried Vitrigel membrane.

Here, examples of a device to which the dried Vitrigel membrane is adhered produced by the production method of the present embodiment include a chamber provided with a dried Vitrigel membrane, the cell enclosure device provided with a dried Vitrigel membrane, and the like, without being limited thereto.

The details of each step of the production method for a device to which the dried Vitrigel membrane is adhered of the present embodiment will be described below.

<Step 8>

First, the member B is separated from the member A in a state in which the dried Vitrigel membrane obtained through steps 1 to 7 described above is arranged in the member A and the member B. Next, the member C is disposed on the member A. At this time, the recess of the member A and the recess of the member C are concentrically arranged so as to overlap. Overlapping the recess of the member A and the recess of the member C makes it possible to adhere the dried Vitrigel membrane to the cylindrical member via the adhesive layer without shifting.

It is possible to appropriately select the time and environment for adhering the dried Vitrigel membrane and the cylindrical member according to the composition of the adhesive layer. Next, configurations and materials of the member C and the cylindrical member will be described below.

[Member C]

(Shape)

The member C has one or more recesses. In addition, in the recess of the member C, a cylindrical member is detachably inserted.

It is possible to shape the recess of the member C such that it is possible to detachably insert the cylindrical member to be described below. Specifically, the bottom surface of the recess of the member C may be smooth or may not be smooth. In addition, in the recess of the member C, the side surface and the bottom surface may be orthogonal to each other or may not be orthogonal to each other.

The cross-section of the recess of the member C is of substantially equal size to a cross-section of the recess of the member A. Specifically, the area of the cross-section of the recess is preferably 1.0 times or less, more preferably 0.9 times or less, even more preferably 0.8 times or less, and particularly preferably 0.75 times the area of the cross-section of the recess of the member A.

The number of recesses in the member C is preferably the same number as the number of recesses in the member A, for example, 1, 2, 3, 4, 5, 6, 7, 8, 9, 10, 12, 15, 20, and the like, without being limited thereto. Among the above, the number of recesses of the member C is preferably an even number, more preferably 2, 4, 6, or 8, and even more preferably 4, 6, or 8.

In addition, in a case where the member C has two or more recesses, the recesses are preferably arranged at equal intervals in the member C. In addition, in a case where the member C has two or more recesses, the recesses are arranged in the member C at the same intervals as the recesses on the member A. In addition, when the member A and the member C are concentrically arranged, the recess of the member C is arranged to overlap with the recess of the member A.

In addition, in the member C, the height of the recess is not particularly limited and it is possible to appropriately adjust the height according to the height of the cylindrical member to be inserted.

In addition, in the member C, it is possible for the shape of the cross-section of the recess to be the same as the cross-section of the recess of the member A, for example, polygons such as triangles, quadrilaterals (including squares, rectangles, and trapezoids), pentagons, hexagons, heptagons, and octagons; circles, approximate circles, ovals, approximate ovals, semicircles, fan shapes, and the like, without being limited thereto. Among the above, the shape of the cross-section of the recess of the member C is preferably circular.

In addition, in the member C, in a case where the cross-section of the recess is circular, it is possible to set the diameter thereof to be substantially the same as the diameter of the recess of the member A, for example, 2 mm or more and 226 mm or less, for example, 5 mm or more and 72 mm or less, and, for example, 10 mm or more and 23 mm or less.

(Material)

The material of the member C is not particularly limited and is preferably the same as the second material forming the member A for ease of handling. Examples of the material of the member C include the same examples illustrated as the second material of the member A described above.

[Cylindrical Member]

(Shape)

It is possible to appropriately select the shape of the cylindrical member according to the application of the device to be obtained. Examples of the shape include a cylindrical shape, a circular cone, a circular truncated cone, a pyramid, a truncated pyramid, a sphere, a polyhedron (for example, a tetrahedron, a pentahedron, a hexahedron (including cubes), an octahedron, a dodecahedron, an icosahedron, an icositetrahedron, a Kepler-Poinsot polyhedron, or the like), and the like, without being limited thereto.

It is possible for the cross-section of the cylindrical member to be smaller than the cross-section of the recess of the member A. Specifically, the area of the cross-section of the cylindrical member is preferably 0.5 times or more, more preferably 0.6 times or more, even more preferably 0.7 times or more, and particularly preferably 0.75 times the area of the cross-section of the recess of the member A.

It is possible for the outer diameter of the cylindrical member to be smaller than the diameter of the recess of the member A. Specifically, the outer diameter of the cylindrical member is preferably 0.7 times or more, more preferably 0.8 times or more, even more preferably 0.85 times or more, and particularly preferably 0.87 times the diameter of the recess of the member A.

It is possible to appropriately select the height of the cylindrical member according to the application of the device to be obtained.

For example, in the case of producing a cell enclosure device, the height of the cylindrical member is 5 µm or more, preferably 50 µm or more and 15 mm or less, more preferably 100 µm or more and 10 mm or less, and even more preferably 500 µm or more and 2 mm or less.

(Material)

It is possible for the material of the cylindrical member to have liquid tightness. In addition, the material of the cylindrical member may have air permeability or may not have air permeability. In a case where the material of the cylindrical member has air permeability, it is possible to set the oxygen permeability coefficient to, for example, 100 $cm^3/m^2 \cdot 24$ hr·atm or more and 5000 $cm^3/m^2 \cdot 24$ hr·atm or less, for example, 1000 $cm^3/m^2 \cdot 24$ hr·atm or more and 3000 $cm^3/m^2 \cdot 24$ hr·atm or less, and, for example, 1200 $cm^3/m^2 \cdot 24$ hr·atm or more and 2500 $cm^3/m^2 \cdot 24$ hr·atm or less. Furthermore, it is possible to set the carbon dioxide permeability coefficient to, for example, 1000 $cm^3/m^2 \cdot 24$ hr·atm or more and 20,000 $cm^3/m^2 \cdot 24$ hr·atm or less, for example, 3000 $cm^3/m^2 \cdot 24$ hr·atm or more and 15,000 $cm^3/m^2 \cdot 24$ hr·atm or less, and, for example, 5000 $cm^3/m^2 \cdot 24$ hr·atm or more and 10,000 $cm^3/m^2 \cdot 24$ hr·atm or less. In addition, in a case where the material of the cylindrical member does not have air permeability, it is possible to set the oxygen permeability coefficient to, for example, 100 $cm^3/m^2 \cdot 24$ hr·atm or less, and, for example, 50 $cm^3/m^2 \cdot 24$ hr·atm or less. Furthermore, it is possible to set the carbon dioxide permeability coefficient to, for example, 1000 $cm^3/m^2 \cdot 24$ hr·atm or less, and, for example, 500 $cm^3/m^2 \cdot 24$ hr·atm or less.

In addition, as a material of a cylindrical member, in the case of producing a device for handling cells, for example, it is possible to use a material suitable for culturing cells. Specific examples of materials suitable for culturing cells include, but are not limited to, for example, glass materials, elastomer materials, plastics including resin polymers or copolymers, and the like. Examples of glass materials include soda lime glass, Pyrex (registered trademark) glass, Vycor (registered trademark) glass, quartz glass, and the like. Examples of elastomer materials include urethane rubber, nitrile rubber, silicone rubber, silicone resins (for example, polydimethylsiloxane), fluororubber, acrylic rubber, isoprene rubber, ethylene propylene rubber, chlorosulfonated polyethylene rubber, epichlorohydrin rubber, chloroprene rubber, styrene butadiene rubber, butadiene rubber, polyisobutylene rubber, and the like. Examples of resin polymers include poly(vinyl chloride), poly(vinyl alcohol), poly(methyl methacrylate), poly(vinyl acetate-co-maleic anhydride), poly(dimethylsiloxane) monomethacrylate, cyclic olefin polymers, fluorocarbon polymers, polystyrene, polypropylene, polyethylenimine, and the like. Examples of copolymers include poly(vinyl acetate-co-maleic anhydride), poly(styrene-co-maleic anhydride), poly(ethylene-co-acrylic acid), derivatives thereof, and the like.

In addition, the cylindrical member has an adhesive layer on the surface which adheres to the dried Vitrigel membrane. As the adhesive forming the adhesive layer, it is possible to use an adhesive having no cytotoxicity, and an adhesive of a synthetic compound may be used or an adhesive of a natural compound may be used. Examples of adhesives of synthetic compounds include urethane adhesives, cyanoacrylate adhesives, polymethyl methacrylate (PMMA), calcium phosphate adhesives, resin cements, and the like. Examples of adhesives of natural compounds include fibrin glue, gelatin glue, and the like. In addition, the adhesive layer may be formed of double-sided tape. As the double-sided tape, it is possible to use a tape having no cytotoxicity and tapes used in medical applications or the like are suitably used. Specific examples thereof include tapes having a structure in which a pressure-sensitive adhesive layer is laminated on both sides of a support and the pressure-sensitive adhesive layer is formed of a known pressure-sensitive adhesive which is rubber-based, acryl-based, urethane-based, silicone-based, or vinyl ether-based, or the like. More specific examples thereof include double-sided tape for attachment to skin (product numbers: 1510, 1504 XL, 1524, and the like) manufactured by 3M Japan Ltd., double-sided pressure-sensitive adhesive tape for skin (product numbers: ST 502, ST 534, and the like) manufactured by Nitto Denko Corporation, double-sided medicinal tape (product numbers: #1088, #1022, #1010, #809 SP, #414125, #1010 R, #1088 R, #8810 R, #2110 R, and the like) manufactured by Nichiban Medical Corp., thin type foam based double-sided adhesive tape manufactured by DIC Corp., (product numbers: #84010, #84015, #84020, and the like), and the like.

<Step 9>

Next, a device to which the dried Vitrigel membrane is adhered is obtained by separating the member A and the member C and extracting the cylindrical member to which the dried Vitrigel membrane is adhered from the member A.

Second Embodiment

The production method for a device to which the dried Vitrigel membrane is adhered of the present embodiment may be further provided with step 10 to step 12 below in this order after step 9.

In step 10, the cylindrical member to which the dried Vitrigel membrane obtained in step 9 is adhered is detachably inserted in the second member C such that the surface to which the dried Vitrigel membrane is adhered is in contact with the bottom surface. Next, an adhesive layer is formed on the peripheral part of the surface of the cylindrical member to which the dried Vitrigel membrane is not adhered. In step 11, first, a second dried Vitrigel membrane is obtained by the production method for a dried Vitrigel membrane according to the above embodiment. Next, the second member B is separated from the second member A in a state where the obtained second dried Vitrigel membrane is formed in the second member A and the second member B. Next, the second member C obtained in step 10 is concentrically arranged such that the recess of the second member A and the recess of the second member C overlap. Next, the second member A is disposed on the second member C such that the adhesive layer on the surface of the second member C to which the Vitrigel dry body is not adhered and the second dried Vitrigel formed in the second member A come in contact. In step 12, the second member C and the second member A are separated and the cylindrical member to which the dried Vitrigel membrane is adhered on both surfaces is extracted from the second member A.

Up to step 8, the steps are the same as the first embodiment described above. A detailed description of the subsequent steps 10 to 12 will be given below.

<Step 10>

The device in which the dried Vitrigel membrane obtained in step 9 is adhered to the cylindrical member is detachably inserted in the second member C such that the surface to which the dried Vitrigel membrane is adhered is in contact with the bottom surface. The second member C is the same as the member C described above.

Next, an adhesive layer is formed on the peripheral part of the surface of the cylindrical member to which the dried Vitrigel membrane is not adhered.

Examples of the formation method of the adhesive layer include a method of coating an adhesive agent, a method of attaching a double-sided tape, and the like, without being limited thereto. Examples of the adhesive and the double-sided tape include the same examples illustrated in step 8 described above.

<Step 11>

Next, a second dried Vitrigel membrane is produced on the second member A using the production method for a dried Vitrigel membrane according to the embodiment described above. Next, the second member B is separated from the second member A in a state where the obtained second dried Vitrigel membrane is formed in the second member A and the second member B. The second member A and the second member B are the same as the member A and the member B described above.

Next, the second member A is disposed on the second member C. At this time, the cylindrical member is detachably inserted in the second member C. This cylindrical member has an adhesive layer at the peripheral part of the surface to which the dried Vitrigel membrane is not adhered. In addition, this cylindrical member has a dried Vitrigel membrane on the surface on the opposite side to the surface of the cylindrical member which has an adhesive layer. In addition, the recess of the second member A and the recess of the second member C are concentrically arranged so as to overlap. Overlapping the recess of the second member C and the recess of the second member A makes it possible to adhere the dried Vitrigel membrane to the cylindrical member via the adhesive layer without shifting. It is possible to appropriately select the time and environment for adhering the dried Vitrigel membrane and the cylindrical member according to the composition of the adhesive layer.

<Step 12>

Next, separating the second member C and the second member A and extracting the cylindrical member with the dried Vitrigel membrane adhered to both surfaces from the second member A makes it possible to obtain a device in which the dried Vitrigel membrane adheres to both surfaces.

<<Production Apparatus for Dried Vitrigel Membrane>>

The production apparatus for a dried Vitrigel membrane of the present embodiment is provided with the member A and the member B. The member A has one or more recesses. In a bottom surface of the recess, a central part is formed of a first material having low adsorptivity to a hydrogel and a peripheral part is formed of a second material having high adsorptivity to a hydrogel. The member B has one or more through holes. The cross-section of the through hole is of substantially equal size to a cross-section of the recess of the member A. In addition, in a case where the member A and the member B are concentrically arranged, the recess and the through hole are arranged so as to overlap.

According to the production apparatus for a dried Vitrigel membrane of the present embodiment, it is possible to produce a dried Vitrigel membrane having a smooth surface without wrinkles in a simple manner.

Figure 1B:
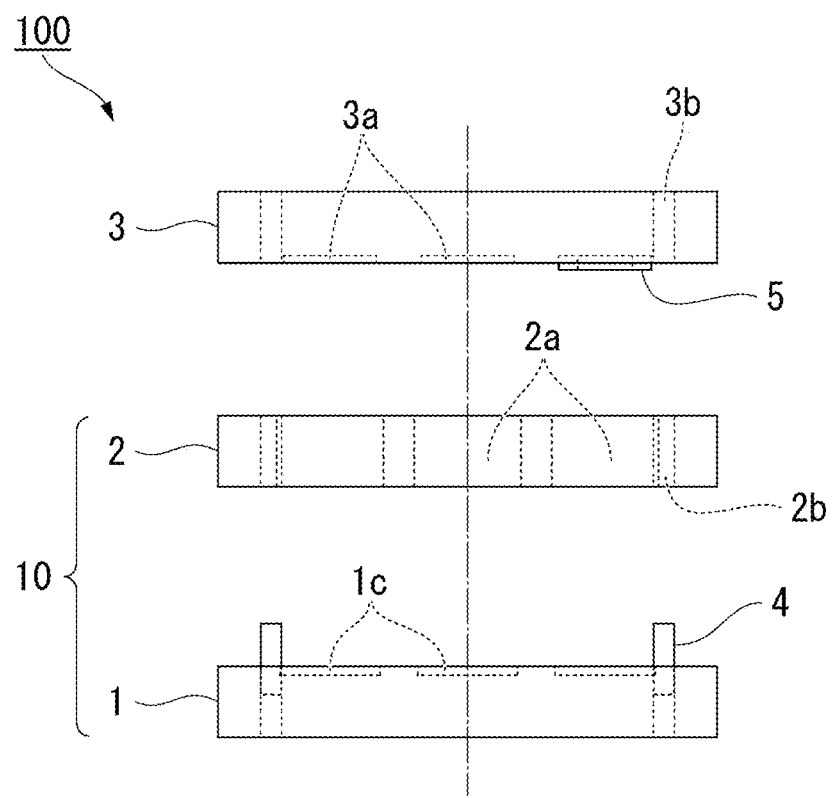
FIG. 1B is a front view showing the example of a production apparatus for a device to which the dried Vitrigel membrane is adhered of the present embodiment.

FIG. 1A is a plan view showing an example of the production apparatus for a device to which a dried Vitrigel membrane is adhered of the present embodiment. In addition, FIG. 1B is a front view showing an example of the production apparatus for a device to which the dried Vitrigel membrane is adhered of the present embodiment. In addition, FIG. 1C is a perspective view showing an example of the production apparatus for a device to which the dried Vitrigel membrane is adhered of the present embodiment.

Figure 1C:
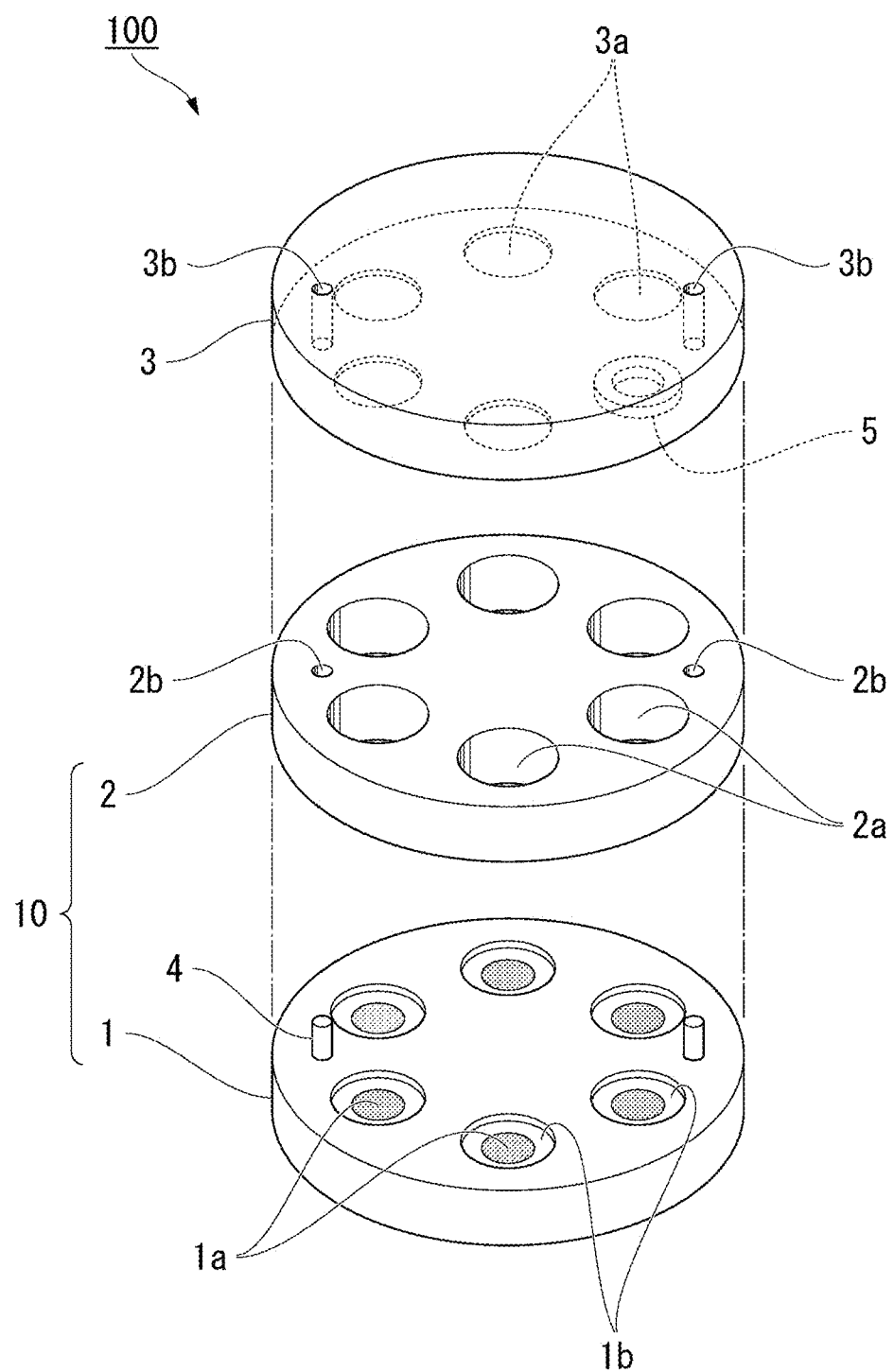
FIG. 1C is a perspective view showing the example of a production apparatus for a device to which the dried Vitrigel membrane is adhered of the present embodiment.

In FIG. 1A to FIG. 1C, a production apparatus for a dried Vitrigel membrane (10) is provided with a member A (1) and a member B (2).

The member A (1) has one or more recesses (1c). In addition, in the bottom surface of the recess (1c), the central part is formed of a first material (1a) having low adsorptivity with respect to a hydrogel. In addition, in the bottom surface of the recess (1c), the peripheral part is formed of a second material (1b) having high adsorptivity with respect to a hydrogel.

Here, the details of the shape of the recess in the member A, a first material, a second material, and the like are as explained in the production method for a dried Vitrigel membrane described above.

In addition, the first material (1a) may be removable at the bottom surface of the recess (1c). At this time, the first material (1a) is preferably adhered to the material forming the bottom surface of the recess (1c) of the member A (1) with a weak force to be easily removable by being physically torn off. Specifically, for example, as shown in the Production Example described below, it is possible to adhere the first material (1a) to the material forming the bottom surface of the recess (1c) of the member A (1) with a weak force to be easily removable by being physically torn off with tweezers or the like via a salt such as PBS. Alternatively, it is possible to adhere the first material (1a) to the material forming the bottom surface of the recess (1c) of the member A (1) with a weak force to be easily removable by physical peeling with tweezers or the like via a release agent layer containing a release agent such as silicone.

At this time, examples of the material forming the bottom surface of the recess (1c) of the member A (1) which presents below the first material (1a) include the same material as the second material described above.

In addition, the member A (1) may have a positioning pin (4) for concentrically arranging the member A (1) and the member B (2) such that the recess (1c) of the member A (1) and a through hole (2a) of the member B (2) overlap. Having the positioning pin (4) makes it possible to concentrically arrange the member A (1) and the member B (2) in a simple manner such that the recess (1c) and the through hole (2a) overlap.

In addition, the member B (2) has one or more through holes (2a). The cross-sections of the through holes (2a) are of substantially equal size to a cross-section of the recess (1c). Specifically, the area of the cross-section of the through hole (2a) is preferably 1 times or more to 1.5 times or less, more preferably 1 times or more to 1.3 times or less, even more preferably 1 times or more to 1.25 times or less, and particularly preferably 1.21 times the area of the cross-section of the recess (1c) of the member A (1).

Here, the details of the shape of the through hole in the member B, the material of the member B, and the like are as explained in the "production method for a dried Vitrigel membrane" described above. In addition, the member B (2) may have a receiving hole (2b) for a positioning pin for concentrically arranging the member A (1) and the member B (2) such that the recess (1c) of the member A (1) and the through hole (2a) of the member B (2) overlap. Having the receiving hole (2b) for the positioning pin makes it possible to concentrically arrange the member A (1) and the member B (2) in a simple manner such that the recess (1c) and the through hole (2a) overlap.

The production apparatus for a dried Vitrigel membrane of the present embodiment is not limited to the examples shown in FIG. 1A to FIG. 1C, but may be a device in which the configuration of a part of the device shown in FIG. 1A to FIG. 1C is changed or removed or a device in which another configuration is further added to the devices described above, within a range which does not impair the effects of the production apparatus for a dried Vitrigel membrane of the present embodiment. For example, in FIG. 1A to FIG. 1C, although the cross-section of the recess of the member A and the cross-section of the through hole of the member B are illustrated as being circular, the cross-sections may take other shapes without being limited thereto. Examples of the shape of the cross-section include the same examples illustrated in the production method for a dried Vitrigel membrane described above. In addition, for example, in FIG. 1A to FIG. 1C, the number of the recesses of the member A and the number of through holes of the member B are illustrated as six; however, without being limited thereto, the numbers may be other numbers such as 1, 2, 3, 4, 5, 6, 7, 8, 9, 10, 12, 15, or 20. In addition, for example, in FIG. 1A to FIG. 1C, the shapes of the member A and the member B are illustrated as cylindrical shapes; however, without being limited thereto, the shapes may be other shapes such as a circular truncated cone, a truncated pyramid, a polyhedron (for example, a tetrahedron, a pentahedron, a hexahedron (including cubes), an octahedron, a dodecahedron, an icosahedron, or an icositetrahedron).

<Other Configuration>

In addition, the production apparatus for a dried Vitrigel membrane of the present embodiment may be further provided with a member D provided with one or more cylindrical blades. It is possible to set the number of cylindrical blades to a number corresponding to the number of recesses of the member A.

In the member D, when the member A and the member D are concentrically arranged, the cylindrical blades are arranged such that the recesses of the member A and the cylindrical blades overlap. Using this member D makes it possible to easily cut off the dried Vitrigel membrane produced in the recess of the member A.

<<Production Apparatus for Device to which Dried Vitrigel Membrane is Adhered>>

First Embodiment

The production apparatus for a device to which the dried Vitrigel membrane is adhered of the present embodiment is provided with the production apparatus for a dried Vitrigel membrane according to the embodiment described above and the member C. The member C has one or more recesses. The cross-section of the recess is of substantially equal size to a cross-section of the recess of the member A. In addition, the recess of the member C is for detachably inserting the cylindrical member which is the main body of the device to which the dried Vitrigel membrane is adhered. In addition, in the production apparatus for a device to which the dried Vitrigel membrane is adhered of the present embodiment, in a case where the member A and the member C are concentrically arranged, the recess of the member A and the recess of the member C are arranged so as to overlap.

According to the production apparatus for a device to which the dried Vitrigel membrane is adhered of the present embodiment, it is possible to continuously produce the device to which the dried Vitrigel membrane is adhered from the production apparatus for a dried Vitrigel membrane.

FIG. 1A is a plan view showing an example of the production apparatus for a device to which a dried Vitrigel membrane is adhered of the present embodiment. In addition, FIG. 1B is a front view showing an example of the production apparatus for a device to which the dried Vitrigel membrane is adhered of the present embodiment. In addition, FIG. 1C is a perspective view showing an example of the production apparatus for a device to which the dried Vitrigel membrane is adhered of the present embodiment.

In FIG. 1A to FIG. 1C, the production apparatus (100) for a device to which the dried Vitrigel membrane is adhered is provided with the production apparatus for a dried Vitrigel membrane (10) and a member C (3). The production apparatus for a dried Vitrigel membrane (10) is as explained in "Production Apparatus for Dried Vitrigel membrane" described above.

The member C (3) has one or more recesses (3a). The cross-section of the recess (3a) is of substantially equal size to a cross-section of the recess (1c) of the member A (1). Specifically, the area of the cross-section of the recess (3a) is preferably 1.0 times or less, more preferably 0.9 times or less, even more preferably 0.8 times or less, and particularly preferably 0.75 times the area of the cross-section of the recess (1c).

Here, the details of the shape of the recess in the member C, the material of the member C, and the like are as explained in the production method for a device to which the dried Vitrigel membrane is adhered described above. In addition, the member C (3) may have a receiving hole (3b) for a positioning pin for concentrically arranging the member A (1) and the member C (3) such that the recess (1c) of the member A (1) and the recess (3a) of the member C (3) overlap. Having the receiving hole (3b) of the positioning pin makes it possible to concentrically arrange the member A (1) and the member C (3) in a simple manner such that the recess (1c) and the recess (3a) overlap.

In addition, it is possible to detachably insert a cylindrical member (5) which is the main body of the device to which the dried Vitrigel membrane is adhered in the recess (3a) of the member C (3). Due to this, it is possible to extract the device to which the produced dried Vitrigel membrane is adhered in a simple manner.

Here, the details of the shape, the material, and the like of the cylindrical member are as explained in the "Production Method for Device to which Dried Vitrigel membrane Is Adhered" described above.

Second Embodiment

The production apparatus for a device to which the dried Vitrigel membrane is adhered of the present embodiment may be provided with two or more of the production apparatuses for a dried Vitrigel membrane according to the embodiment described above.

The production apparatus for a device to which the dried Vitrigel membrane is adhered of the present embodiment has the same configuration as the production apparatus for a device to which the dried Vitrigel membrane is adhered of the first embodiment described above except for being provided with two or more of the production apparatuses for a dried Vitrigel membrane.

Providing two or more production apparatuses for a dried Vitrigel membrane makes it possible to produce a device in which the dried Vitrigel is adhered to both surfaces in a simple manner.

Examples of the number of production apparatuses for a dried Vitrigel membrane include 2, 3, 4, 5, 6, 7, 8, 9, 10, 15, 20, and the like, without being limited thereto. Among the above, the number of production apparatuses for a dried Vitrigel membrane is preferably an even number, so that it is possible to produce the dried Vitrigel membrane on two surfaces at the same time.

EXAMPLES

The present invention will be described below using Examples; however, the present invention is not limited to the following Examples.

[Production Example 1] Production of Dried Native Collagen Vitrigel Membrane 1

(1) Preparation of Production Apparatus

In order to produce dried Vitrigel membranes, a production apparatus (manufactured by Kishimoto Industry Co., Ltd., formed of acrylic resin) shown in FIG. 1A to FIG. 1C was used. Specifically, a member A with a thickness of 10 mm (recess: a depth of 1.0 mm and a circular bottom surface with a diameter of 15.0 mm), a member B with a thickness of 5 mm (a through hole: a circular shape with a diameter of 16.5 mm), and a member C with a thickness of 5 mm (recess: a depth of 0.75 mm and a circular bottom surface with a diameter of 13.03 mm) were used. In addition, as a material having low adsorptivity to collagen Vitrigel, a polyvinyl chloride film (manufactured by Unipack, AS ONE 6-633-25, thickness 0.08 mm) was used. First, the polyvinyl chloride film was punched into a $\phi$13 mm circle using a punching machine. Next, the obtained circular polyvinyl chloride film was placed in a $\phi$60 mm petri dish holding a 70% ethanol solution, immersed for 10 minutes, and sterilized. After 10 minutes, the 70% ethanol solution was removed and washing was carried out by adding PBS. The washing was repeated 3 times.

Next, a 70% ethanol solution was sprayed onto the member A and the member B formed of acrylic resin to carry out sterilization and drying was carried out in a clean bench. Next, a double-sided tape (manufactured by Scotch, thickness 0.065 mm) was attached to the surface of one side of the polyvinyl chloride film and the side to which the double-sided tape was attached was adhered to the bottom surface of the recess of the member A. Polyvinyl chloride films were similarly adhered to all six wells of the member A.

Next, the member A and the member B were made to overlap using a positioning pin. Next, while the member A and the member B were held, Parafilm (registered trademark) was wrapped around the periphery and two weights (50 t×25×25, approximately 260 g, manufactured by Kishimoto Industry Co., Ltd. Co., Ltd.) were placed on the member B.

(2) Preparation of Collagen Sol 2 mL of a bovine serum-containing culture medium was dispensed into a 50 mL conical tube on ice. Subsequently, 2 mL of a bovine-derived native collagen solution (manufactured by Koken Co., Ltd., I-AC, collagen concentration 0.5 mass %) was added thereto and pipetting was performed three times to prepare a uniform collagen sol. The bovine serum-containing culture medium which was used had the composition shown below.

Bovine serum-containing culture medium: Dulbecco's Modified Eagle's Medium (DMEM) (manufactured by GIBCO, Cat. No. 11885-084)

Inactivated fetal bovine serum (Fetal Bovine Serum; FBS) (manufactured by SIGMA, F2442)

20 mM HEPES (manufactured by GIBCO, Cat. No. 15630-080)

100 units/mL penicillin+100 μg/mL streptomycin (manufactured by GIBCO, Cat. No. 15140-148)

(3) Pouring of Collagen Sol

Next, 800 μL of collagen sol was poured onto the polyvinyl chloride film adhered to the bottom surface of the member A from the through hole of member B, the collagen sol was allowed to spread throughout the well, then 440 μL was removed and 360 μL of collagen sol in the well was allowed to remain. Next, the same operation was repeated six times for all six wells while moving the weights.

(4) Gelation of Collagen

Next, the member into which the collagen sol was poured in (3) was stored for 2 hours in an incubator with a 5% carbon dioxide concentration set at 37° C. to cause gelation. After gelation, the weights were removed.

(5) Vitrification of Collagen Gel (Production of Dried Collagen Gel)

Next, after gelation, drying was carried out by blowing air in a thermostatic and humidistatic chamber set at 10° C. and 40% humidity to carry out vitrification and obtain a dried collagen gel.

(6) Rehydration of Dried Collagen Gel (Production of Vitrigel)

Next, after vitrification, the result was taken out from the thermostatic and humidistatic chamber and weights were placed on the member B again. Next, 1 mL of PBS was added thereto from the through holes of the member B and allowed to stand for 10 minutes to carry out rehydration (first addition of PBS). After 10 minutes, the PBS was removed, and 1 mL of PBS was added again from the through hole of the member B, and allowed to stand for 10 minutes (second addition of PBS). The same operation was performed again (third addition of PBS), the PBS was removed, and rehydration was completed.

(7) Re-Vitrification of Vitrigel (Production of Dried Vitrigel)

After rehydration, drying was carried out by blowing air in a thermostatic and humidistatic chamber set at 10° C. and 40% humidity to carry out re-vitrification and obtain a dried Vitrigel.

(8) Punching of Dried Vitrigel

Next, after re-vitrification, the result was taken out from the thermostatic and humidistatic chamber and a portion covered on the top surface of the member A in the dried Vitrigel was cut using a punching blade (manufactured by Morishita Seihan Ltd., φ15.4 mm). Next, it was confirmed that the cutting was carried out using a punching blade, the member B was removed from the member A, and a dried Vitrigel membrane was produced on the member A.

[Production Example 2] Production of Cell Enclosure Device Provided with Dried Native Collagen Vitrigel Membrane 1

(1) Production of Dried Vitrigel Membrane 1

A dried Vitrigel membrane was produced on the member A using the same method as in (1) to (8) in Production Example 1.

(2) Preparation of Cylindrical Member 40 mL of sterile water was added to a 50 mL conical tube. Then, a ring formed of polystyrene (manufactured by Kishimoto Industry Co., Ltd., inner diameter 7.98 mm, outer diameter 13 mm, thickness 2.0 mm) was added as a cylindrical member which was the main body of the cell enclosure device and washing was carried out by shaking for 10 minutes on a shaker (manufactured by NISSIN, RECIPRO SHAKER). After washing, the sterile water was removed, 40 mL of new sterile water was added thereto, and the same operation was repeated three times. Next, 40 mL of a 70% ethanol solution was added to the 50 mL conical tube, the ring washed with sterile water was added thereto, and sterilization was carried out by shaking for 3 minutes on a shaker (manufactured by NISSIN, RECIPRO SHAKER).

(3) Coating of Adhesive on Cylindrical Member and Mounting on Member C 1

First, a 70% ethanol solution was sprayed on a member C formed of an acrylic resin to carry out sterilization and drying was carried out in a clean bench. Next, a suitable amount of a polyurethane adhesive (UM700, manufactured by Cemedine Co., Ltd.) was taken using a 200 μL long tip and the adhesive was spread on the peripheral part of the ring. Next, the ring was mounted on the member C in a state in which it was detachably inserted such that the surface of the ring to which the adhesive was not coated was in contact with the bottom surface of the member C.

(4) Adhesion of Cylindrical Member and Dried Vitrigel Membrane 1

Next, in a state in which the dried Vitrigel membrane obtained in (1) was produced, the member A was overlapped on the member C on which the ring was mounted using a positioning pin such that the surface of the ring on which the adhesive was coated and the dried Vitrigel membrane were in contact. Next, a weight was placed on the member A and allowed to stand for one day in a clean bench to dry the adhesive.

(5) Removal of Member C 1

One day after the start of drying, the dryness was confirmed, the ring was turned upside down such that the member C faced upwards, and the member C was removed. Next, using tweezers, the ring to which the dried Vitrigel membrane was adhered was pushed and shifted from the side and slowly detached from the bottom surface of the well of the member A. Next, the ring in which the dried Vitrigel membrane was adhered to one surface was placed in a φ60 mm petri dish. Next, Parafilm (registered trademark) was wrapped on the petri dish, which was protected from light by aluminum foil and stored at room temperature.

(6) Production of Dried Vitrigel Membrane 2

Dried Vitrigel membranes were produced on another set of members A using the same methods as in (1) to (8) in Production Example 1.

(7) Coating of Adhesive on Cylindrical Member and Mounting on Member C 2

The ring in which the dried Vitrigel membrane was adhered to one surface stored in (5) was extracted from the petri dish and an adhesive was spread on the peripheral part of the surface on the opposite side to the surface to which the dried Vitrigel membrane was adhered. Next, the ring in which the dried Vitrigel membrane was adhered to one surface was mounted on the member C so as to be detachably inserted such that the surface of the ring to which the dried Vitrigel membrane of the ring was adhered and the bottom surface of the member C were in contact.

(8) Adhesion of Cylindrical Member and Dried Vitrigel Membrane 2

Next, in a state in which the dried Vitrigel membrane obtained in (6) was produced, the member A was overlapped on the member C on which the ring was mounted, using a positioning pin such that the surface of the ring on which the adhesive was coated and the dried Vitrigel membrane were in contact. Next, a weight was placed on the member A and allowed to stand for one day in a clean bench to dry the adhesive.

(9) Removal of Member C 2

One day after the start of drying, the dryness was confirmed, the ring was turned upside down such that the member C faced upwards, and the member C was removed. Next, using tweezers, the ring to which the dried Vitrigel membrane was adhered was pushed and shifted from the side and slowly detached from the bottom surface of the well of the member A to obtain a ring in which a dried Vitrigel membrane was adhered to both surfaces (that is, a cell enclosure device). Next, the obtained ring in which the dried Vitrigel membrane was adhered to both surfaces (cell enclosure device) was placed in a 35 mm petri dish and Parafilm (registered trademark) was wrapped around the petri dish, which was protected from light by aluminum foil and stored at room temperature.

[Production Example 3] Production of Dried Native Collagen Vitrigel Membrane 2

(1) Preparation of Production Apparatus

As a material having low adsorptivity with respect to collagen Vitrigel, a silicone-treated polyethylene terephthalate (PET) film (thickness of 75 µm, manufactured by Fujimori Kogyo Co., Ltd.) was used. First, the silicone-treated PET film was punched out using a punching machine to a circle of φ13 mm Next, the silicone-treated surface was confirmed by attaching a mending tape (manufactured by Scotch, thickness 0.058 mm) on the obtained circular silicone-treated PET film. Next, the obtained circular silicone-treated PET film was placed in a φ60 mm petri dish holding a 70% ethanol solution and immersed for 10 minutes to carry out sterilization. After 10 minutes, the 70% ethanol solution was removed and PBS was added to carry out washing while being careful about the surface. The washing was repeated 3 times.

Next, a 70% ethanol solution was sprayed onto a 24-well plate (manufactured by Kishimoto Industry Co., Ltd., formed of acrylic resin) having wells formed of a circular bottom surface with a depth of 5.0 mm and a diameter of 15.0 mm to carry out sterilization. Next, drying was carried out in a clean bench. Next, the washed silicone-treated PET films were placed one by one on the bottom surface of the 24-well plate such that the silicone-treated surface was the upper surface. Next, 1 mL of PBS was added thereto and removed and drying was carried out in a clean bench for approximately 3 hours to weakly adhere the silicone-treated PET film to the bottom surface of the 24-well plate via the salt of PBS.

(2) Preparation of Collagen Sol

A uniform collagen sol was prepared using the same method as in (2) in Production Example 1.

(3) Pouring of Collagen Sol

Next, 600 µL of collagen sol was poured on the silicone-treated PET film in a 24-well plate, the collagen sol was allowed to spread throughout the wells, then 240 µL was removed and 360 µL of collagen sol in the well was allowed to remain. Next, the same operation was repeated 24 times for all 24 wells.

(4) Gelation of Collagen

Next, the 24-well plate into which the collagen sol was poured in (3) was stored for 2 hours in an incubator at a 5% carbon dioxide concentration set at 37° C. to carry out gelation.

(5) Vitrification of Collagen Gel (Production of Dried Collagen Gel)

Next, after gelation, drying was carried out by blowing air in a thermostatic and humidistatic chamber set at 10° C. and 40% humidity to carry out vitrification and obtain a dried collagen gel.

(6) Rehydration of Dried Collagen Gel (Production of Vitrigel)

Next, after vitrification, the result was taken out from the thermostatic and humidistatic chamber, and 600 µL of PBS was added to the wells, and allowed to stand for 10 minutes to carry out rehydration (the first addition of PBS). After 10 minutes, the PBS was removed, and 600 µL of PBS was again added to the wells and allowed to stand for 10 minutes (the second addition of PBS). The same operation was performed again (the third addition of PBS), the PBS was removed, and rehydration was completed.

(7) Re-Vitrification of Vitrigel (Production of Dried Vitrigel)

After rehydration, drying was carried out by blowing air in a thermostatic and humidistatic chamber set at 10° C. and 40% humidity to carry out re-vitrification and obtain a dried Vitrigel attached on the silicone-treated PET film.

(8) Removal of Dried Vitrigel Adsorbed to Film from 24-Well Plate

Tweezers were inserted into a gap between a well inner wall surface of the 24-well plate and the PET film such that the PET film was removed from the bottom surface of the well by being pushed weakly and shifted from the side. As a result, a dried native collagen Vitrigel membrane having a smooth surface without wrinkles, to which the silicone-treated PET film was weakly attached, was obtained. The weak attachment of the silicone-treated PET film was confirmed as follows. First, a mending tape was attached on the surface of the PET film on the side to which the dried native collagen Vitrigel membrane was not attached. Thereafter, a mending tape was also attached on the surface of the dried native collagen Vitrigel membrane on the opposite side, to which the PET film was not attached. Next, it was confirmed that it was possible to very easily remove the PET film and the dried native collagen Vitrigel membrane by weakly pulling the mending tapes on both sides away from each other.

Example 1

Figure 2A:
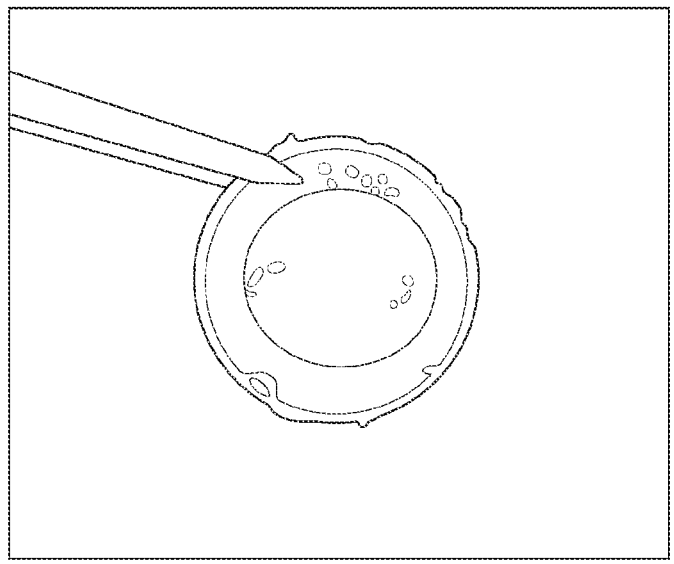
FIG. 2A is an image showing a state in which a cell enclosure device obtained using a production method for a device to which the dried Vitrigel membrane is adhered according to the present embodiment is filled with PBS in Example 1.

The inside of a ring on which a dried Vitrigel membrane was adhered to both surfaces obtained in Production Example 2 (cell enclosure device) was filled with PBS. The results are shown in FIG. 2A. As seen in FIG. 2A, the Vitrigel membrane in the cell enclosure device in a state in which PBS was poured therein had a uniform, smooth surface without wrinkles.

Comparative Example 1

Figure 2B:
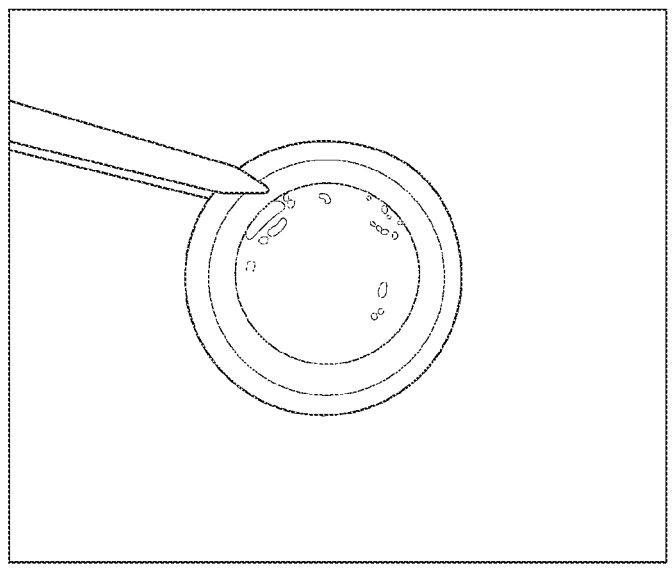
FIG. 2B is an image showing a state in which a cell enclosure device to which the dried Vitrigel membrane produced using a ring-shaped magnet is adhered is filled with PBS in Comparative Example 1.

A dried Vitrigel membrane was produced by a method using two ring-shaped magnets (reference document: Japanese Patent No. 4817847), which is a production method of the related art. Next, a ring in which the dried Vitrigel membrane was adhered to both surfaces (cell enclosure device) was produced by adhering the obtained dried Vitrigel membrane to a ring using a polyurethane adhesive. Next, the inside of the cell enclosure device was filled with PBS. The results are shown in FIG. 2B. As seen in FIG. 2B, the Vitrigel membrane in the cell enclosure device in a state in which PBS was poured therein had slight wrinkles at the peripheral part.

The results of Example 1 and Comparative Example 1 show that using the production method and production apparatus for a dried Vitrigel membrane of the present embodiment makes it possible to produce a dried Vitrigel membrane having a smooth surface without wrinkles in a simple manner.

[Production Example 4] Production of Dried Atelocollagen Vitrigel Membrane 1

(1) Preparation of Production Apparatus

A production apparatus was prepared using the same method as in (1) in Production Example 1.

(2) Preparation of Collagen Sol

Next, 4 mL of a serum-free culture medium was dispensed into a 50 mL conical tube on ice. Next, 4 mL of a porcine-derived atelocollagen solution (manufactured by Kanto Chemical Co., Inc., collagen concentration: 1.0% by mass) was added thereto and pipetting was performed three times to prepare a uniform collagen sol. The serum-free culture medium which was used had the composition shown below.

Serum-free culture medium: Dulbecco's Modified Eagle's Medium (DMEM) (manufactured by GIBCO, Cat. No. 11885-084)

20 mM HEPES (GIBCO, Cat. No. 15630-080)

100 units/mL penicillin+100 μg/mL streptomycin (manufactured by GIBCO, Cat. No. 15140-148)

(3) Pouring of Collagen Sol

Next, 900 μL of collagen sol was poured from the through holes of the member B onto a polyvinyl chloride film adhered to the bottom surface of the member A to spread the collagen sol throughout the wells. Next, the same operation was repeated six times for all six wells while moving the weight.

(4) Gelation of Collagen

The collagen was gelled using the same method as in (4) in Production Example 1.

(5) Vitrification of Collagen Gel (Production of Dried Collagen Gel)

The collagen gel was vitrified using the same method as in (5) in Production Example 1.

(6) Rehydration of Dried Collagen Gel (Production of Vitrigel)

The dried collagen gel was rehydrated using the same method as in (6) in Production Example 1.

(7) Re-vitrification of Vitrigel (Production of Dried Vitrigel)

The Vitrigel was re-vitrified using the same method as in (7) in Production Example 1.

(8) Punching Out of Dried Vitrigel

Dried Vitrigel membranes were produced on the member A using the same method as in (8) in Production Example 1.

[Production Example 5] Production of Chamber Provided with Dried Atelocollagen Vitrigel Membrane (1) Production of Dried Vitrigel Membrane Dried Vitrigel membranes were produced on the member A using the same method as in (1) to (8) in Production Example 4.

(2) Preparation of Cylindrical Member

An acrylic pipe (inner diameter: φ11 mm, outer diameter: φ15 mm, length: 15 mm) was used as a cylindrical member as the main body of a chamber. In a peripheral part of the acrylic pipe, the outer diameter on one surface was processed using a file to taper to approximately 14 mm Next, two acrylic hangers were adhered to the peripheral part of the pipe on the non-tapered side. After adhesion, the cylindrical member was placed in a 50 mL conical tube in which 40 mL of sterile water had been poured in advance. Next, washing was carried out by shaking for 10 minutes on a shaker (manufactured by NISSIN, RECIPRO SHAKER). After washing, the sterile water was removed, 40 mL of new sterile water was added thereto, and the same operation was repeated three times. Next, 40 mL of a 70% ethanol solution was added to a 50 mL conical tube, a pipe washed with sterile water was introduced thereinto, and sterilization was carried out by shaking for 3 minutes on a shaker (manufactured by NISSIN, RECIPRO SHAKER).

(3) Adhesion of Double-Sided Tape to Cylindrical Member

A thin type foam based double-sided adhesive tape (manufactured by DIC Corp., #84010 WHITE, thickness 100 μm) was cut into a ring-shaped shape (inner diameter φ11 mm and outer diameter φ14 mm). Next, one side of the cut double-sided tape was adhered to the peripheral part of the pipe on the tapered side and an adhesive layer was formed on the peripheral part of the pipe.

(4) Adhesion of Cylindrical Member and Dried Vitrigel Membrane

Next, a pipe in which a double-sided tape was adhered to the peripheral part of one side was overlapped and adhered on the dried Vitrigel membrane on the obtained member A in (1) such that the surface to which the double-sided tape was adhered in the peripheral part of the pipe and the dried Vitrigel membrane were in contact. Next, the pipe was slowly detached from the bottom surface of the member A to produce a chamber provided with a dried Vitrigel membrane.

Example 2

Figure 3:
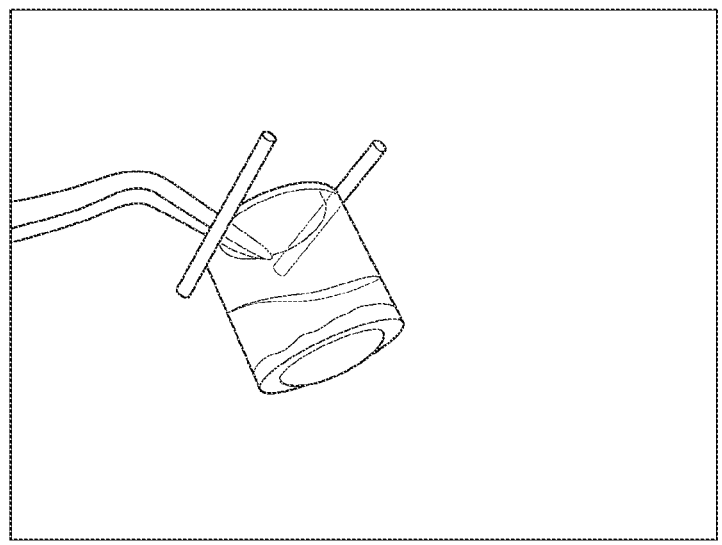
FIG. 3 is an image showing a state in which PBS is poured into a chamber to which the dried Vitrigel membrane is adhered of the present embodiment in Example 2.

PBS was poured into the inside of the pipe (chamber) obtained in Production Example 4 in which the dried Vitrigel membrane was adhered to one surface. The results are shown in FIG. 3. From FIG. 3, it was confirmed that PBS does not leak from the Vitrigel membrane in the chamber in a state where PBS was poured therein.

[Production Example 6] Production of Dried Atelocollagen Vitrigel Membrane 2

(1) Preparation of Production Apparatus

A silicone-treated polyethylene terephthalate (PET) film (thickness 75 μm, manufactured by Fujimori Kogyo Co., Ltd.) was used as a material having a low adsorptivity with respect to collagen Vitrigel. First, the silicone-treated PET film was punched into a φ13 mm circle using a punching machine. Next, the silicone-treated surface was confirmed by attaching a mending tape (manufactured by Scotch, thickness 0.058 mm) on the obtained circular silicone-treated PET film. Next, the obtained circular silicone-treated PET film was placed in a φ60 mm petri dish holding a 70% ethanol solution and immersed for 10 minutes to carry out sterilization. After 10 minutes, the 70% ethanol solution was removed and PBS was added to carry out washing while being careful about the surface. The washing was repeated 3 times.

In order to produce dried Vitrigel membranes, a production apparatus (manufactured by Kishimoto Industry Co., Ltd., formed of acrylic resin) shown in FIG. 1A to FIG. 1C was used. Specifically, a member A with a thickness of 10 mm (recess: a depth of 1.0 mm and a circular bottom surface with a diameter of 15.0 mm) and a member B with a thickness of 5 mm (a through hole: a circular shape with a diameter of 16.5 mm) were used. Next, a 70% ethanol solution was sprayed on the member A and member B formed of an acrylic resin to carry out sterilization and drying was carried out in a clean bench.

Next, the washed silicone-treated PET films were then placed, one by one, on the bottom of all six wells of the member A, such that the silicone-treated surface was on top. Next, approximately 0.5 mL of PBS at a time was added and removed and drying was carried out in a clean bench for approximately 3 hours to weakly adhere the silicone-treated PET film on the bottom surface of the wells of the member A via the salt of PBS. Next, the member A and the member B were made to overlap using a positioning pin. Next, while holding the member A and the member B, Parafilm (registered trademark) was wrapped around the periphery and two weights (50 t×25×25, approximately 260 g, manufactured by Kishimoto Industry Co., Ltd. Co., Ltd.) were placed on the member B.

(2) Preparation of Collagen Sol

A uniform collagen sol was prepared using the same method as in (2) in Production Example 4.

(3) Pouring of Collagen Sol

Next, 900 μL of collagen sol was poured onto the silicone-treated PET film adhered to the bottom surface of the member A from the through holes of the member B and the collagen sol was spread throughout the wells. Next, the same operation was repeated six times for all six wells while moving the weights.

(4) Gelation of Collagen

The collagen was gelled using the same method as in (4) in Production Example 1.

(5) Vitrification of Collagen Gel (Production of Dried Collagen Gel)

The collagen gel was vitrified using the same method as in (5) in Production Example 1.

(6) Rehydration of Dried Collagen Gel (Production of Vitrigel)

The dried collagen gel was rehydrated using the same method as in (6) in Production Example 1.

(7) Re-Vitrification of Vitrigel (Production of Dried Vitrigel)

The Vitrigel was re-vitrified using the same method as in (7) in Production Example 1.

(8) Removal of Dried Vitrigel Adsorbed to Film from Member A

A dried Vitrigel membrane was produced on the member A using the same method as in (8) in Production Example 1. Next, tweezers were inserted into a gap between a well inner wall surface of the member A and the PET film such that the PET film was removed from the bottom surface of the well by being pushed weakly and shifted from the side. As a result, a dried atelocollagen Vitrigel membrane having a smooth surface without wrinkles, to which the silicone-treated PET film was weakly attached, was obtained.

Figure 4:
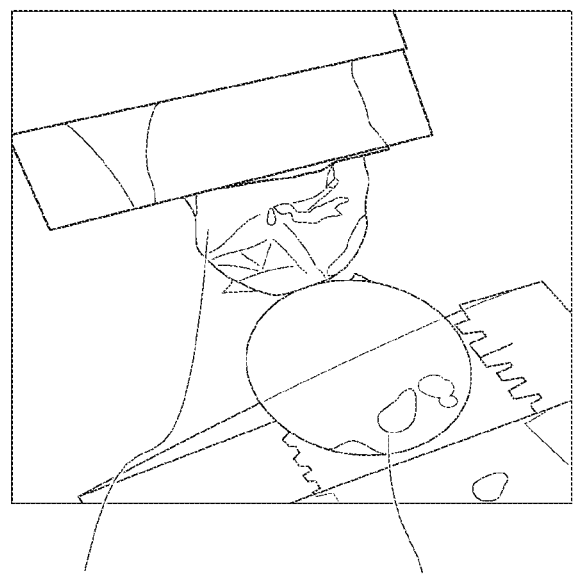
FIG. 4 is an image showing the manner in which the dried Vitrigel membrane of the present embodiment and a PET film are detached in Production Example 6.

Here, the weak attachment of the silicone-treated PET film was confirmed as follows. First, a mending tape was attached on the surface of the PET film on the side to which the dried atelocollagen Vitrigel membrane was not attached. Next, a mending tape was also attached on the surface of the dried atelocollagen Vitrigel membrane on the side to which the PET film was not attached, which was the opposite side. Next, it was confirmed that it was possible to easily remove the PET film and the dried atelocollagen Vitrigel membrane by weakly pulling the mending tapes on both sides away from each other (refer to FIG. 4).

[Production Example 7] Production of Cell Enclosure Device Provided with Dried Native Collagen Vitrigel Membrane 2

(1) Production of Dried Vitrigel Membrane

Dried Vitrigel membranes were produced on the member A using the same method as in (1) to (8) in Production Example 1.

(2) Preparation of Cylindrical Member

Using the same method as in (2) of Production Example 2, a polystyrene ring (manufactured by Kishimoto Industry Co., Ltd. Co., Ltd., inner diameter ϕ7.98 mm, outer diameter ϕ13 mm, and thickness 2.0 mm) was prepared.

(3) Mounting of Cylindrical Member on Member C and Adhesion of Double-Sided Tape to Cylindrical Member 1

First, a thin foam base waterproof double-sided tape (manufactured by Nitto Denko Corporation, No. 57210 B, thickness: 0.1 mm) was punched into a ring shape with a punching machine using a punching blade (ϕ12 mm and ϕ8.5 mm). Two sheets were prepared. Next, a 70% ethanol solution was sprayed on a member C formed of an acrylic resin to carry out sterilization and drying was carried out in a clean bench. Next, the ring was placed on the member C. Next, one of the ring shapes punched out from the double-sided tape was attached to the ring placed on the member C so as not to protrude from the ring.

(4) Adhesion of Cylindrical Member and Dried Vitrigel Membrane 1

Next, a release paper of the surface of the double-sided tape on the side which was not in contact with the ring was peeled off to expose a pressure-sensitive adhesive layer. Next, the member C on which the ring was placed and the member A in a state in which the dried Vitrigel membrane obtained in (1) was produced were overlapped using a positioning pin such that the surface on which the pressure-sensitive adhesive layer of the ring was exposed and the dried Vitrigel membrane were in contact and the ring and the dried Vitrigel membrane were adhered.

(5) Detachment of Member C 1

Next, the ring was turned upside down such that the member C faced upwards, and the member C was removed. Next, using tweezers, the ring to which the dried Vitrigel membrane was adhered was pushed and shifted from the side and slowly detached from the bottom surface of the well of the member A.

(6) Production of Dried Vitrigel Membrane 2

Dried Vitrigel membranes were produced on another set of members A using the same methods as in (1) to (8) in Production Example 1.

(7) Mounting of Cylindrical Member on Member C and Adhesion of Double-Sided Tape to Cylindrical Member 2

Next, the ring to which the dried Vitrigel membrane was adhered on one surface produced in (5) was placed on the member C. Next, the double-sided tape punched into a ring shape in (3) was adhered on the surface on the opposite side to the surface to which the dried Vitrigel membrane of the ring was adhered, so as not to protrude from the ring.

(8) Adhesion of Cylindrical Member and Dried Vitrigel Membrane 2

Next, a release paper on the surface of the double-sided tape which was not in contact with the ring was peeled off to expose a pressure-sensitive adhesive layer. Next, the member C on which the ring to which the dried Vitrigel membrane was adhered on one side was placed and the member A in a state in which the dried Vitrigel membrane obtained in (6) was produced were overlapped using a positioning pin such that the surface on which the pressure-sensitive adhesive layer of the ring was exposed and the dried Vitrigel membrane were in contact and the ring and the dried Vitrigel membrane were adhered.

(9) Detachment of Member C 2

Next, the ring was turned upside down such that the member C faced upwards and the member C was removed. Next, using tweezers, the ring to which the dried Vitrigel membrane was adhered was pushed and shifted from the side and slowly detached from the bottom surface of the well of the member A to obtain a ring in which a dried Vitrigel membrane was adhered to both surfaces (that is, a cell enclosure device). Next, the obtained ring in which the dried Vitrigel membrane was adhered to both surfaces (cell enclosure device) was placed in a 35 mm petri dish and Parafilm (registered trademark) was wrapped around the petri dish, which was protected from light by aluminum foil and stored at room temperature.

[Production Example 8] Production of Cell Enclosure Device Provided with Dried Native Collagen Vitrigel Membrane 3

(1) Production of Dried Vitrigel Membrane

Dried Vitrigel membranes were produced on the member A using the same method as in (1) to (8) in Production Example 1.

(2) Preparation of Cylindrical Member

A silicone rubber sheet (thickness: 2 mm, product number: 2-9318-01, produced by As One Corporation) was punched out using a $\phi$13 mm and $\phi$8 mm punching blade to produce a silicone ring. Next, the produced silicone ring was immersed in 70% ethanol for 10 minutes and then sterilized by washing three times with PBS.

(3) Mounting of Cylindrical Member on Member C and Adhesion of Double-Sided Tape to Cylindrical Member 1

First, a double-sided adhesive tape for silicone rubber adhesion (manufactured by Nitto Denko Corporation, No. 5302A, thickness: 0.085 mm) was punched into a ring shape with a punching machine using a punching blade ($\phi$12 mm and $\phi$8.5 mm). Two sheets were prepared. Next, a 70% ethanol solution was sprayed on a member C formed of an acrylic resin to carry out sterilization and drying was carried out in a clean bench. Next, a silicone ring was placed on the member C. Next, one of the ring shapes punched out from the double-sided tape was attached to the ring so as not to protrude from the ring. At this time, the surface (release paper: transparent side) of the pressure-sensitive adhesive layer for silicone rubber adhesion of the double-sided tape was attached to the silicone ring.

(4) Adhesion of Cylindrical Member and Dried Vitrigel Membrane 1

Next, a release paper on the surface of the double-sided tape of the side which was not in contact with the silicone ring was peeled off to expose a pressure-sensitive adhesive layer. Next, the member C on which the ring was placed and the member A in a state in which the dried Vitrigel membrane obtained in (1) was produced were overlapped using a positioning pin such that the surface on which the pressure-sensitive adhesive layer of the ring was exposed and the dried Vitrigel membrane were in contact and the silicone ring and the dried Vitrigel membrane were adhered.

(5) Detachment of Member C 1

Next, the ring was turned upside down such that the member C faced upwards and the member C was removed. Next, using tweezers, the silicone ring to which the dried Vitrigel membrane was adhered was pushed and shifted from the side and slowly detached from the bottom surface of the well of the member A.

(6) Production of Dried Vitrigel Membrane 2

Dried Vitrigel membranes were produced on another set of the members A using the same method as in (1) to (8) in Production Example 1.

(7) Mounting of Cylindrical Member on Member C and Adhesion of Double-Sided Tape to Cylindrical Member 2

Next, the silicone ring to which the dried Vitrigel membrane was adhered on one surface produced in (5) was placed on the member C. Next, a double-sided tape for silicone rubber adhesion punched into a ring shape in (3) was adhered on the surface on the opposite side to the surface of the silicone ring to which the dried Vitrigel membrane was adhered, so as not to protrude from the ring. At this time, the surface (release paper: transparent side) of the pressure-sensitive adhesive layer for silicone rubber adhesion of the double-sided tape was attached to the silicone ring.

(8) Adhesion of Cylindrical Member and Dried Vitrigel Membrane 2

Next, a release paper of the surface of the double-sided tape on the side which was not in contact with the silicone ring was peeled off to expose a pressure-sensitive adhesive layer. Next, the member C on which the silicone ring was placed and the member A in a state in which the dried Vitrigel membrane obtained in (6) was produced were overlapped using a positioning pin such that the surface on which the pressure-sensitive adhesive layer of the silicone ring was exposed and the dried Vitrigel membrane were in contact and the silicone ring and the dried Vitrigel membrane were adhered.

(9) Detachment of Member C 2

Next, the ring was turned upside down such that the member C faced upwards and the member C was removed. Next, using tweezers, the silicone ring to which the dried Vitrigel membrane was adhered was pushed and shifted from the side and slowly detached from the bottom surface of the well of the member A, and a silicone ring to which the dried Vitrigel membrane was adhered on both surfaces (that is, a cell enclosure device) was obtained. Next, the obtained silicone ring in which the dried Vitrigel membrane was adhered to both surfaces (cell enclosure device) was placed in a petri dish of $\phi$35 mm, and Parafilm (registered trademark) was wrapped around the petri dish, which was protected from light by aluminum foil and stored at room temperature.

[Production Example 9] Production of Cell Enclosure Device Formed of Dried Atelocollagen Vitrigel Membrane (1) Preparation of Production Apparatus In order to produce dried Vitrigel membranes, a production apparatus (manufactured by Kishimoto Industry Co., Ltd., formed of acrylic resin) shown in FIG. 1A to FIG. 1C was used. Specifically, a member A with a thickness of 10 mm (recess: a depth of 1.0 mm and a circular bottom surface with a diameter of 15.0 mm) and a member B with a thickness of 5 mm (a through hole: a circular shape with a diameter of 16.5 mm) were used. Next, a 70% ethanol solution was sprayed on the member A and the member B formed of an acrylic resin to carry out sterilization and drying was carried out in a clean bench.

Next, the wall surface in the recess of the member A was wiped using a KimWipe impregnated with silicone oil (KF-96, manufactured by Shin-Etsu Chemical Co., Ltd.). Next, the member A and the member B were made to overlap using a positioning pin. Next, Parafilm (registered trademark) was wrapped around the periphery while holding the member A and the member B.

(2) Preparation of Collagen Sol

A uniform collagen sol was prepared using the same method as in (2) in Production Example 4.

(3) Production of Dried Vitrigel Membrane

Using the same method as in (3) to (7) in Production Example 4 except for using the production apparatus prepared in (1), 1.8 mL of collagen sol was poured on the bottom surface of the member A from the through hole of member B to produce a dried atelocollagen Vitrigel membrane on the member A.

(4) Preparation of Cylindrical Member

A cylindrical member formed of atelocollagen was prepared using a known method (reference document 1: WO 2018/003858). Specifically, the cylindrical member was produced by the procedure shown below.

(4-1) Production of Dried Atelocollagen Vitrigel Membrane

First, 28 mL of 0.5% atelocollagen sol was poured into a mold with a wall surface having an inner diameter of 60 mm, and eight dried atelocollagen Vitrigel membranes (collagen content: 5.0 mg/cm$^2$) were produced by a known method (reference document 2: WO 2012/026531). In addition, after dispensing 16 mL of serum-free culture medium to a 50 mL conical tube on ice, 0.5% atelocollagen sol was prepared by adding 16 mL of a porcine-derived atelocollagen solution (manufactured by Kanto Chemical Co., Inc., collagen concentration: 1.0% by mass) and performing pipetting three times.

(4-2) Production of Dried Atelocollagen Vitrigel Membrane Double Layer Adhesive Body Next, two atelocollagen Vitrigel membranes were prepared by rehydrating two dried atelocollagen Vitrigel membranes with PBS. One sheet of an atelocollagen Vitrigel membrane was stretched on a vinyl sheet. Next, 600 μL of 0.5% atelocollagen sol was added thereon and spread so as not to protrude from the membrane and then one more sheet of an atelocollagen Vitrigel membrane was covered thereon. Here, 0.5% atelocollagen sol was used as an adhesive according to a known method (reference document 3: Japanese Unexamined Patent Application, First Publication No. 2015-203018). Next, drying (vitrification) was carried out using a clean air dryer in an incubator at 10° C. and 40% humidity. Next, UV irradiation (total UV irradiation amount per unit area: 400 mJ/cm$^2$) was performed. Furthermore, the double layer adhesive dried body after UV irradiation was turned over and UV irradiation (total UV irradiation amount per unit area: 400 mJ/cm$^2$) was performed to obtain a dried atelocollagen Vitrigel membrane double layer adhesive body.

(4-3) Production of Dried Atelocollagen Vitrigel Membrane Quadruple Layer Adhesive Body Next, the dried atelocollagen Vitrigel membrane double layer adhesive body obtained in (4-2) was rehydrated with PBS. Next, one double layer adhesive body was stretched on a vinyl sheet. Next, 600 μL of 0.5% atelocollagen sol was added thereon and spread so as not to protrude from the double layer adhesive body and then one more double layer adhesive body was covered thereon to produce a quadruple layer adhesive body. Next, drying (vitrification) was carried out using a clean air dryer in an incubator at 10° C. and 40% humidity. Next, UV irradiation (total UV irradiation amount per unit area: 400 mJ/cm$^2$) was performed. Furthermore, the dried quadruple layer adhesive after UV irradiation was turned over and UV irradiation (total UV irradiation amount per unit area: 400 mJ/cm$^2$) was performed to obtain a dried atelocollagen Vitrigel membrane quadruple layer adhesive body.

(4-4) Molding of Cylindrical Member

Next, the dried atelocollagen Vitrigel membrane quadruple layer adhesive body obtained in (4-3) was punched out at two points with a φ13 mm and φ8 mm punching blade and two ring-shaped dried atelocollagen Vitrigel membrane quadruple layer adhesives (inner diameter 8 mm and outer diameter 13 mm) were produced.

(5) Adhesion of Cylindrical Member and Dried Vitrigel

First, the dried atelocollagen Vitrigel membrane on the member A produced in (3) was rehydrated with PBS to prepare an atelocollagen Vitrigel membrane. On the other hand, the ring-shaped dried atelocollagen Vitrigel membrane quadruple layer adhesive produced in (4) was similarly rehydrated with PBS to prepare a ring-shaped atelocollagen Vitrigel membrane quadruple layer adhesive body. Next, a ring-shaped atelocollagen Vitrigel membrane quadruple layer adhesive body was stretched on a vinyl sheet. Then, 20 μL of 0.5% atelocollagen sol was added onto the quadruple layer adhesive body and spread so as not to protrude from the ring. Next, the ring-shaped atelocollagen Vitrigel membrane quadruple layer adhesive body and the atelocollagen Vitrigel membrane were adhered such that the surface on which the atelocollagen sol of the ring-shaped atelocollagen Vitrigel membrane quadruple layer adhesive body was coated was in contact with the atelocollagen Vitrigel membrane on the member A. Next, using a clean air dryer in an incubator at 10° C. and 40% humidity, drying (vitrification) was carried out to obtain a ring-shaped atelocollagen Vitrigel membrane quadruple layer adhesive body provided with an atelocollagen Vitrigel membrane on one surface (which may be referred to below as a "ring-shaped quadruple layer adhesive body with a single surface membrane"). Two of these ring-shaped quadruple layer adhesive bodies with single surface membranes were produced. Next, the two ring-shaped quadruple layer adhesive dried bodies with single surface membranes were each detached from the members A. Next, UV irradiation (total UV irradiation amount per unit area: 400 mJ/cm$^2$) was performed on the surface of the ring-shaped quadruple layer adhesive dried bodies with single surface membranes on the side in contact with the member A. Furthermore, after the UV irradiation, the ring-shaped quadruple layer adhesive dried bodies with single surface membranes were turned over and UV irradiation (total UV irradiation amount per unit area: 400 mJ/cm$^2$) was also performed on the surface on the side to which the ring-shaped atelocollagen Vitrigel membrane quadruple layer adhesive dried body was adhered.

(6) Adhesion of Ring-Shaped Quadruple Layer Adhesive Bodies with Single Surface Membranes Next, the two ring-shaped quadruple layer adhesive dried bodies with single surface membranes obtained in (5) were rehydrated with PBS to obtain ring-shaped quadruple layer adhesive bodies with single surface membranes. Next, on a vinyl sheet, the two ring-shaped quadruple layer adhesive bodies with single surface membranes were stretched such that the surface on the side to which each of the ring-shaped atelocollagen Vitrigel membrane quadruple layer adhesive bodies was adhered was on top. Next, 20 μL of 0.5% atelocollagen sol was added to one of the ring-shaped quadruple layer adhesive body with single surface membrane and spread so as not to protrude from the ring. Next, the ring-shaped quadruple layer adhesive body with a single surface membrane on which atelocollagen sol was coated and one more ring-shaped quadruple layer adhesive body with a single surface membrane on which atelocollagen sol was not coated were adhered such that the surfaces on the side to which the quadruple layer adhesive bodies were adhered were in contact. Next, drying (vitrification) was carried out using a clean air dryer in an incubator at 10° C. and 40% humidity. Next, UV irradiation (total UV irradiation amount per unit area: 400 mJ/cm$^2$) was performed. Furthermore, the result was turned over and UV irradiation (total UV irradiation amount per unit area: 400 mJ/cm$^2$) was performed to obtain a cell enclosure device formed of a dried atelocollagen Vitrigel membrane. Next, the obtained cell enclosure device formed of the dried atelocollagen Vitrigel membrane was placed in a $\phi$35 mm petri dish, Parafilm (registered trademark) was wrapped around the petri dish, which was protected from light by aluminum foil and stored at room temperature.

INDUSTRIAL APPLICABILITY

According to the production method and production apparatus for a dried Vitrigel membrane of the present embodiment, it is possible to produce a dried Vitrigel membrane having a smooth surface without wrinkles in a simple manner. In addition, according to the production method and production apparatus for a device to which the dried Vitrigel membrane is adhered of the present embodiment, it is possible to continuously produce the device to which dried Vitrigel membrane is adhered from the production method and production apparatus for a dried Vitrigel membrane.

REFERENCE SIGNS LIST

1: Member A,
1$a$: First material,
1$b$: Second material,
1$c$: Recess of member A,
2: Member B,
2$a$: Through hole,
2$b$: Receiving hole of positioning pin in member B,
3: Member C,
3$a$: Recess of member C,
3$b$: Receiving hole of positioning pin in member C,
4: Positioning pin,
5: Cylindrical member,
10: Production apparatus for dried Vitrigel membrane,
100: Production apparatus for device to which dried Vitrigel membrane is adhered

The invention claimed is:

1. A production method for a dried Vitrigel film, the method comprising, in the following order:
    step 1 of concentrically arranging and disposing a member A, which has one or more recesses and in which, in a bottom surface of the recess, a central part of the bottom surface is formed of a first material having low adsorptivity to a hydrogel and a peripheral part of the bottom surface is formed of a second material having high adsorptivity to a hydrogel, and a member B having one or more through holes with a cross-section of substantially equal size to a cross-section of the recess of the member A, such that the recess of the member A and the through hole of the member B overlap;
    step 2 of pouring a sol from the through holes of member B;
    step 3 of gelling the sol by leaving the member A and the member B in which the sol is poured to stand;
    step 4 of drying and vitrifying a hydrogel obtained in step 3 in a state in which it is formed in the member A and the member B;
    step 5 of hydrating the dried hydrogel obtained in step 4 in a state in which it is formed in the member A and the member B;
    step 6 of drying and re-vitrifying the Vitrigel obtained in step 5 in a state in which it is formed in the member A and the member B; and
    step 7 of cutting off a portion slightly covering a top surface of the member A from the dried Vitrigel obtained in step 6 using a cylindrical blade of which the cross-section is a size slightly larger than the cross-section of the recess of the member A and slightly smaller than the cross-section of the through hole of the member B.

2. The production method for a dried Vitrigel film according to claim 1, wherein the first material is removable at the bottom surface of the recess of the member A.

* * * * *